(12) United States Patent
Dias et al.

(10) Patent No.: US 9,737,637 B2
(45) Date of Patent: Aug. 22, 2017

(54) METHOD FOR REDUCING THE AMOUNT OF MIGRATEABLES OF POLYMER COATINGS

(75) Inventors: Aylvin Jorge Angelo Athanasius Dias, Maastricht (NL); Marnix Rooijmans, Born (NL); Victor Litvinov, Beek (NL); Edwin Peter Kennedy Currie, Sittard (NL); Erwin Johannes Elisabeth Houben, Maastricht (NL)

(73) Assignee: DSM IP ASSETS B.V., Heerlen (NL)

( * ) Notice: Subject to any disclaimer, the term of this patent is extended or adjusted under 35 U.S.C. 154(b) by 1466 days.

(21) Appl. No.: 11/791,488

(22) PCT Filed: Nov. 28, 2005

(86) PCT No.: PCT/EP2005/012864
§ 371 (c)(1),
(2), (4) Date: Mar. 3, 2008

(87) PCT Pub. No.: WO2006/056482
PCT Pub. Date: Jun. 1, 2006

(65) Prior Publication Data
US 2008/0306455 A1    Dec. 11, 2008

(30) Foreign Application Priority Data
Nov. 29, 2004    (EP) .................................... 04078245

(51) Int. Cl.
| | | |
|---|---|---|
| *B05D 3/02* | (2006.01) | |
| *A61L 29/08* | (2006.01) | |
| *A61L 27/34* | (2006.01) | |
| *A61L 31/10* | (2006.01) | |

(52) U.S. Cl.
CPC ............. *A61L 29/085* (2013.01); *A61L 27/34* (2013.01); *A61L 31/10* (2013.01)

(58) Field of Classification Search
CPC ........ A61L 27/34; A61L 31/10; A61L 29/085; B05D 3/06; B05D 5/08
See application file for complete search history.

(56) References Cited

U.S. PATENT DOCUMENTS

| | | | |
|---|---|---|---|
| 4,105,519 | A | 8/1978 | Pennewiss et al. |
| 4,111,922 | A | 9/1978 | Beede et al. |
| 4,117,184 | A | 9/1978 | Erickson et al. |

(Continued)

FOREIGN PATENT DOCUMENTS

| | | |
|---|---|---|
| EP | 0 289 996 | 11/1988 |
| EP | 0 405 464 | 1/1991 |

(Continued)

OTHER PUBLICATIONS

International Search Report mailed Mar. 23, 2006 in PCT/EP2005/012864.

(Continued)

*Primary Examiner* — Robert S Walters, Jr.
(74) *Attorney, Agent, or Firm* — Nixon & Vanderhye P.C.

(57) ABSTRACT

This invention relates to an improved process for obtaining a cross-linked polymer coating on a surface. The invention also relates to coatings obtainable by that process and objects coated therewith. The invention also relates to medical devices comprising a coating, in particular to coils coated with an improved lubricious coating.

20 Claims, 11 Drawing Sheets

(56) References Cited

U.S. PATENT DOCUMENTS

Figure 1:
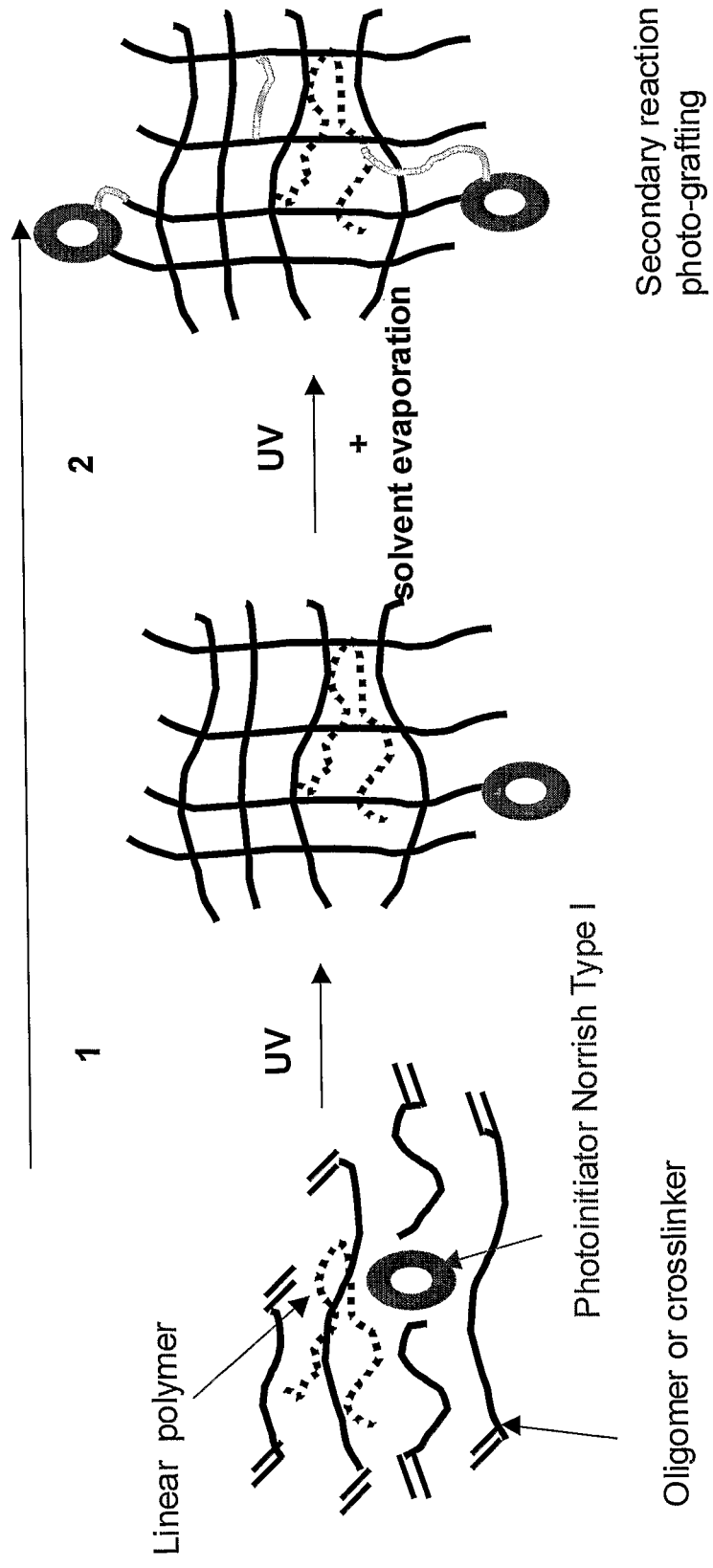

| | | |
|---|---|---|
| 4,272,620 A | 6/1981 | Ichimura |
| 4,612,336 A | 9/1986 | Yada et al. |
| 4,818,325 A | 4/1989 | Hiraiwa et al. |
| 4,874,822 A | 10/1989 | Rasmussen et al. |
| 4,876,126 A | 10/1989 | Takemura et al. |
| 5,005,287 A | 4/1991 | Ritter |
| 5,008,301 A | 4/1991 | Dennis et al. |
| 5,077,352 A | 12/1991 | Elton |
| 5,084,315 A | 1/1992 | Karimi et al. |
| 5,091,205 A | 2/1992 | Fan |
| 5,126,189 A | 6/1992 | Tanny et al. |
| 5,135,516 A | 8/1992 | Sahatjian et al. |
| 5,317,063 A | 5/1994 | Komatsu et al. |
| 5,670,557 A | 9/1997 | Dietz |
| 5,700,559 A | 12/1997 | Sheu et al. |
| 5,702,754 A | 12/1997 | Zhong |
| 5,756,144 A | 5/1998 | Wolff et al. |
| 5,804,318 A | 9/1998 | Pinchuk et al. |
| 5,985,990 A | 11/1999 | Kantner et al. |
| 5,994,419 A | 11/1999 | Collette et al. |
| 6,048,620 A | 4/2000 | Zhong |
| 6,110,451 A | 8/2000 | Matz et al. |
| 6,120,904 A | 9/2000 | Hostettler et al. |
| 6,221,425 B1 | 4/2001 | Michal et al. |
| 6,238,799 B1* | 5/2001 | Opolski ............ 428/423.1 |
| 6,310,116 B1 | 10/2001 | Yasuda et al. |
| 6,565,981 B1 | 5/2003 | Messner et al. |
| 6,589,665 B2 | 7/2003 | Chabrecek et al. |
| 6,673,053 B2 | 1/2004 | Wang et al. |
| 6,709,706 B2 | 3/2004 | Zhong et al. |
| 6,720,130 B1 | 4/2004 | Zhong et al. |
| 6,835,783 B1 | 12/2004 | Gartner et al. |
| 6,849,685 B2 | 2/2005 | Soerens et al. |
| 6,887,961 B2 | 5/2005 | Soerens et al. |
| 7,264,859 B2 | 9/2007 | Rouns et al. |
| 7,544,381 B2 | 6/2009 | Kangas |
| 8,809,411 B2 | 8/2014 | Rooijmans |
| 2001/0011165 A1 | 8/2001 | Engelson et al. |
| 2001/0027299 A1 | 10/2001 | Yang et al. |
| 2002/0002353 A1 | 1/2002 | Michal et al. |
| 2002/0004140 A1 | 1/2002 | Swan et al. |
| 2002/0013549 A1 | 1/2002 | Zhong et al. |
| 2003/0013615 A1 | 1/2003 | Levy |
| 2003/0031697 A1* | 2/2003 | Chudzik ............ 424/423 |
| 2003/0031802 A1 | 2/2003 | Weiss et al. |
| 2003/0096131 A1 | 5/2003 | Beavers et al. |
| 2004/0019168 A1 | 1/2004 | Soerens et al. |
| 2004/0043688 A1 | 3/2004 | Soerens et al. |
| 2004/0110861 A1 | 6/2004 | Shorbu et al. |
| 2004/0135967 A1 | 7/2004 | Carney et al. |
| 2004/0143180 A1 | 7/2004 | Zhong et al. |
| 2005/0054774 A1 | 3/2005 | Kangas |
| 2005/0070688 A1* | 3/2005 | Lewandowski ............ 528/425 |
| 2005/0080157 A1 | 4/2005 | Wagener et al. |
| 2005/0100580 A1 | 5/2005 | Osborne et al. |
| 2005/0170071 A1 | 8/2005 | Eramo |
| 2005/0191430 A1 | 9/2005 | Rubner et al. |
| 2006/0240060 A1 | 10/2006 | Bavaro |
| 2007/0167735 A1 | 7/2007 | Zhong et al. |
| 2008/0292776 A1 | 11/2008 | Dias et al. |
| 2009/0169715 A1 | 7/2009 | Dias et al. |
| 2010/0113871 A1 | 5/2010 | Dias et al. |
| 2010/0198168 A1 | 8/2010 | Rooijmans |
| 2011/0059874 A1 | 3/2011 | Rooijmans et al. |

FOREIGN PATENT DOCUMENTS

| | | |
|---|---|---|
| EP | 0 480 809 | 4/1992 |
| EP | 1 065 738 | 1/2001 |
| EP | 1 621 217 | 2/2006 |
| EP | 1 776 968 | 4/2007 |
| JP | 54-147696 | 11/1979 |
| JP | 04-144567 | 5/1992 |
| JP | 5-300940 | 11/1993 |
| JP | 06-039347 | 2/1994 |
| JP | 10-211273 | 8/1998 |
| JP | 10-277144 | 10/1998 |
| JP | 11-172149 | 6/1999 |
| JP | 11-209648 | 8/1999 |
| JP | 2001-000531 | 1/2001 |
| JP | 2004-82713 | 3/2004 |
| JP | 2007-23130 | 2/2007 |
| WO | 93/11751 | 6/1993 |
| WO | WO 94/22596 A | 10/1994 |
| WO | 96/28762 | 9/1996 |
| WO | 97/17378 | 5/1997 |
| WO | 97/29160 | 8/1997 |
| WO | 98/50461 | 11/1998 |
| WO | 98/58989 | 12/1998 |
| WO | 99/38546 | 8/1999 |
| WO | 01/51103 | 7/2001 |
| WO | 01/92584 | 12/2001 |
| WO | 2004/056909 | 7/2004 |
| WO | 2004/060427 | 7/2004 |
| WO | 2004/091685 | 10/2004 |
| WO | WO 2005035607 A1 * | 4/2005 |
| WO | 2006/042514 | 4/2006 |
| WO | 2006/056482 | 6/2006 |
| WO | 2007/065722 | 6/2007 |
| WO | 2008/012325 | 1/2008 |
| WO | 2008/031596 | 3/2008 |
| WO | 2008/071796 | 6/2008 |
| WO | 2008/104573 | 8/2008 |
| WO | 2011/157805 | 12/2011 |

OTHER PUBLICATIONS

Written Opinion mailed Mar. 23, 2006 in PCT/EP2005/012864.
Alt, V. et al., "Plasma Polymer Coating with High-Porosity Silver for Antimicrobial Protection of Osteosynthetic Devices", Osteosynthese International 2005—Kongress, Oral Presentation, No. 075, Sep. 15, 2005, 1 page.
Asha, S. K. et al., "Synthesis and Curing Studies of PPG Based Telechelic Urethane Methacrylic Macromonomers", European Polymer Journal, vol. 41, No. 1, Jan. 2005, pp. 23-33.
Guggenbichler, J.P. et al., "A New Technology of Microdispersed Silver in Polyurethane Induces Antimicrobial Activity in Central Venous Catheters", Infection, vol. 27, Suppl. 1, pp. S16-S23, 1999.
Samuel, U. et al., "Prevention of Catheter-Related Infections: the Potential of a New Nano-Silver Impregnated Catheter", International Journal of Antimicrobial Agents, vol. 23, Suppl. 1, pp. S75-S78, Mar. 2004.
U.S. Appl. No. 13/704,714, filed Dec. 17, 2012.
Database WPI Week 199517, *Thomas Scientific*, XP002451204 & JP 07 053895, Feb. 28, 1995 Abstract.
International Search Report for PCT/EP2008/052396 mailed Feb. 16, 2009.
Written Opinion for PCT/EP2008/052396 mailed Feb. 16, 2009.
International Search Report for PCT/EP2006/011903 dated Aug. 8, 2007.
Written Opinion of the International Searching Authority for PCT/EP2006/011903 dated Aug. 8, 2007.
International Search Report for PCT/EP2006/011904 mailed Mar. 16, 2007.
Written Opinion of the International Searching Authority for PCT/EP2006/011904 mailed Mar. 16, 2007.
International Search Report for PCT/EP2007/007995 mailed Feb. 27, 2008.
Written Opinion of the International Searching Authority for PCT/EP2007/007995 mailed Feb. 27, 2008.
International Search Report for PCT/EP2008/052397 mailed Jan. 13, 2009.
International Search Report for PCT/EP2009/052918 mailed Jun. 22, 2009.
Written Opinion of the International Searching Authority for PCT/EP2009/052918 mailed Jun. 22, 2009.
International Search Report for PCT/EP2006/011902, dated Aug. 6, 2007.
Written Opinion of the International Searching Authority for PCT/EP2006/011902, dated Aug. 6, 2007.

(56) References Cited

OTHER PUBLICATIONS

International Search Report for PCT/EP2007/007984, dated Apr. 11, 2008.
Written Opinion of the International Searching Authority for PCT/EP2007/007984, dated Apr. 11, 2008.
International Search Report for PCT/EP2011/060066, mailed Sep. 5, 2011.
Written Opinion of the International Searching Authority for PCT/EP2011/060066, mailed Sep. 5, 2011.
Japanese Patent Office, Notice of Reasons for Rejection, P2008-543747, Dispatch No. 004257 (Jan. 10, 2012) (English Translation).
Japanese Patent Office, Final Rejection, P2008-543747, Dispatch No. 472881 (Jul. 17, 2012) (English Translation).
JP Office Action with English-Language Translation mailed Dec. 18, 2012, (Appln No. P2009-551200).
JP Office Action with English-Language Translation mailed Dec. 18, 2012, (Appln No. P2009-551201).

\* cited by examiner

METHOD FOR REDUCING THE AMOUNT OF MIGRATEABLES OF POLYMER COATINGS

This application is the U.S. national phase of international application PCT/EP2005/012864 filed 28 Nov. 2005 which designated the U.S. and claims benefit of EP 04078245.0, dated 29 Nov. 2004, the entire content of which is hereby incorporated by reference.

This invention relates to an improved process for obtaining a cross-linked polymer coating on a surface. The invention also relates to coatings obtainable by that process and objects coated therewith. The invention also relates to medical devices comprising a coating, in particular to coils coated with an improved lubricious coating.

People have continually attempted to impart certain functional properties to a surface by applying coatings to it. For instance, a hydrophobic surface may be made hydrophilic by applying a hydrophilic coating to it. In its most simple form a hydrophilic coating consists of a layer of molecules such as hydrophilic polymers that provide the desired hydrophilic properties. A recurrent problem is that such single polymer coatings do not adhere to the surface well enough to resist mechanical or other abrasive forces applied to the surface. A common way of making coatings adhere better to the surface is to add chemically reactive groups to the polymers that can be covalently attached to the surface. However, it is often found that the polymers loose their functional properties when cross-linked to the surface in that way. Also, this method still results in coatings that are not adhered well enough to the surface for particular high-duty applications.

Better results have been achieved by physically entrapping functional polymers into a network of a second supporting polymer that provides the necessary adherence to the surface. In that way the functional properties of the functional polymer are mostly well maintained. These coatings are often referred to as interpenetrating networks or IPNs. IPNs thus consist of a first functional polymer that provides the desired properties to the coating and a supporting polymer that is chemically cross-linked in order to form a network of polymers. An inherent disadvantage of having the functional polymer physically entrapped in the network rather than covalently coupled to the surface is that the functional polymer may migrate out of the IPN into the environment of the coating.

The term "migrateables" as used herein as recognized in the art to indicate molecules that may leak out of a particular matrix under particular circumstances. The term is synonymous with "extractables" or "extractable components" which are also frequently used in the art.

In certain applications where a coating comes into contact with liquids, there is a desire to minimize the amount of migrateables. For example, coatings used in membranes for separations and films for food contact should contain a minimal amount of migrateables. The desire to minimize the amount of migrateables becomes especially pertinent when the coatings are applied to sensitive applications such as in medical applications including medical devices that come into close contact with the body or body fluids such as contact lenses, guide wires and catheters. The loss of one or more components from a coating may result in change in composition and functional properties of the coating as well as contaminating the immediate host environment. Moreover, the migrateable component may be harmful when released into the environment of the coating, such as the food, human body or body fluids.

A number of ways have been described to minimise the migration of polymers out of an IPN coating. One proposed solution is to increase the cross-link density of the supporting polymer, thus resulting in a network with smaller meshes. Increasing the cross-link density of the supporting polymer, however, may result in a brittle coating and/or failure of other mechanical requirements.

Another suggested solution (U.S. Pat. Nos. 4,642,267 and 5,700,559) is to increase the molecular interaction between the cross-linked supporting polymer and the non-cross-linked functional polymer via Van der Waals, hydrogen bonding or electrostatic interactions. However, these methods do not result in sufficient reduction of the amount of migrateables, in particular when the coating is subjected to repeated mechanical perturbation, dramatic temperature changes, solvents, electrolytes, solutions that interfere with the polymer—polymer interactions or circumstances that cause a dramatic swell of the IPN (Leger et al. Micromolecules 1995, 28, 143, J. E Mark et. al. J. Polym. Sci. Polym. Phys. Ed. (1983), 21 1971).

Another solution (U.S. Pat. No 6,224,893) to better entrap the functional polymer in the network is to introduce cross-links between the functional polymers. In that way two intercalating networks (one consisting of the supporting polymer and the other of the functional polymer) are formed that are not chemically attached to each other. Such networks are often referred to as total interpenetrating networks or total IPNs. The chemical procedures involved in making such total IPNs are often complicated and cumbersome, and involve the addition of cross-linkable groups to the functional polymer. A total IPN may provide excellent coatings with a low amount of migrateables, however, it is difficult to achieve due to phase separation, that arises due to differences in polymerization speed of the ingredients or inadequate compatibility between the two networks. Compatibility in this respect refers to the ability of the two polymers to achieve a desired function.

Yet another solution to prevent the functional polymer from migrating out of a lubricious coating consisting of a supporting polymer and a hydrophilic polymer is provided in U.S. Pat. No. 6,238,799. Herein it is suggested to attach reactive groups to the functional polymer, which react into the network of the supporting polymer. It is said that such covalent anchoring may be suitably used with functional polymers that have been polymerized with reactive monomers, such as PVP/RCOOH, PVP or PVOH anhydrides or PVP acetamide. In that way a coating is obtained wherein the functional polymer is chemically cross-linked to the supporting polymer forming the network. However, in this procedure a reactive group has to be attached to the functional polymer via a prior chemical reaction. Moreover, the restriction of the mobility of the functional polymer is said to adversely affect the functional properties of the coating.

Yet another solution has been suggested in WO99/64086 wherein a steel stent is coated with a supporting polymer (polydimethylsiloxane) that has been chemically functionalised with benzophenone, a Norrish type II photoinitiator. After drying of the supporting polymer, a functional polymer (PVP) is then UV cross-linked to the network through hydrogen abstraction. This method requires a dual coating step, which adds to the costs and complexity of the coating procedure.

Photochemical surface modification by Norrish Type II hydrogen abstraction reactions has been applied in U.S. Pat. No. 5,002,583. This approach requires an additional synthetic step where the hydrophilic polymers and biopolymers are modified with a Norrish Type II chromophore (typically diarylketones) prior to grafting onto a surface.

Still, the above-mentioned solutions do not provide entirely satisfactory results, in the sense that they often do not combine the desired ease of handling with a sufficient reduction of the amount of migrateables in order to allow the coatings to be used in applications where low amount of migrateables is desired, such as in the human body.

Surprisingly, it has now been found that particularly good grafting of a functional oligomer or polymer to a supporting monomer, oligomer or polymer network in a solvent may be accomplished by using a Norrish type I photoinitiator to induce polymer crosslinks between the supporting polymer and the functional polymer through a hydrogen abstraction reaction. In other words, the invention concerns the use of a Norrish type 1 photoinitiator to induce polymer cross-linking through a hydrogen abstraction mechanism.

Such may be accomplished by evaporating the solvent in between cross-linking of the supporting monomer, oligomer or polymer. This method has the advantage that it does not require the separate addition of a reactive group to the functional oligomer or polymer, nor the prior impregnation of a surface with a Norrish type II photoinitiator. Yet, the functional oligomer or polymer becomes covalently bound to the supporting network.

The invention therefore relates to a process wherein a coating composition is used comprising
- at least one supporting monomer, oligomer or polymer capable of forming a supporting polymer network
- at least one functional oligomer or polymer
- at least one photoinitiator capable of performing a Norrish type I or homolytic bond cleavage photopolymerisation reaction In one aspect, the invention provides a process comprising the steps of:
- Providing a surface
- Providing at least one supporting monomer, oligomer or polymer capable of forming a network
- Providing at least one functional oligomer or polymer
- Providing at least one photoinitiator capable of performing a Norrish type I or homolytic bond cleavage photopolymerisation reaction
- Mixing said at least one supporting monomer, oligomer or polymer with said at least one functional oligomer or polymer and said at least one photoinitiator with a suitable solvent in order to obtain a coating composition
- Applying said coating composition to said surface.
- Exposing the coating composition on the surface to an energy source suitable to induce cross-linking of said at least one supporting monomer, polymer or oligomer
- Evaporating the solvent
- Exposing the coating composition on the surface to said energy source at least once again.

In another aspect the invention provides a process comprising the steps of:
- Providing a surface
- Providing at least one supporting monomer, oligomer or polymer capable of forming a network
- Providing at least one functional oligomer or polymer
- Providing at least one photoinitiator capable of performing a Norrish type I or homolytic bond cleavage photopolymerisation reaction
- Mixing said at least one supporting monomer, oligomer or polymer with said at least one functional oligomer or polymer and said at least one photoinitiator with a suitable solvent in order to obtain a coating composition
- Applying said coating composition to said surface.
- Exposing the coating composition on the surface to an energy source suitable to induce cross-linking of said at least one supporting monomer, polymer or oligomer, wherein said photoinitiator is used to initiate polymerisation of the supporting monomer, oligomer or polymer in order to form a network and to generate extra cross-links with the functional oligomer or polymers by hydrogen abstraction reaction via the photoinitiator that is bound to the supporting monomer, oligomer or polymer.

Suitable surfaces for use in the invention are surfaces that provide the desired properties such as porosity, hydrophobicity, hydrophilicity, colorisability, strength, flexibility, permeability, elongation abrasion resistance and tear resistance. Examples of suitable surfaces are for instance surfaces that consist of metals, plastics and ceramics. Objects that are particularly suited to be used as a surface in the present invention include catheters, guidewires, stents, metal and plastic implants, contact lenses and medical tubing.

A suitable supporting monomer, oligomer or polymer for use in the invention comprises a plurality of functional moieties capable of undergoing cross-linking reactions, said supporting monomer, oligomer or polymer being soluble in or emulsified in a medium such as an aqueous based medium. When crosslinked at the functional moieties, the supporting monomer, oligomer or polymer is capable of forming a three-dimensional network. The functional moiety of the supporting monomer, oligomer or polymer may be selected from the group consisting of radically reactive groups, such as amino, amido, sulphhydryl (SH), unsaturated esters, ethers and amides, alkyd/dry resins. In a preferred embodiment, the supporting monomer, oligomer or polymer may be selected from the group consisting of polyethers, poly(meth)acrylates, polyurethanes, polyethylene and polypropylene co-difunctional polymers, polyvinyl chlorides, epoxides, polyamides, polyesters like polyorthoesters and alkyd copolymers. More in particular, a suitable supporting monomer, oligomer or polymer is selected from the group consisting of polyesters, polyethers, polyamides, polypeptides, polyacrylics or polysaccharides such as cellulose and starch. In particular, supporting monomer, oligomer or polymers with unsaturated esters, amides or ethers, thiol or mercaptan groups may suitably be used in the invention.

The supporting monomer, oligomer or polymer should be used in more than 0% of the coating composition, preferably more than 1 such as 2%. The supporting monomer, oligomer or polymer can be present in the coating composition up to 90%, however, more often the supporting monomer, oligomer or polymer will be used up to 50, 60, 70 or 80%. A typical range for the content of the supporting monomer, oligomer or polymer in the coating solution is 1-20%.

As used herein, the term monomer refers to molecules with a molecular weight of less than approximately 1000 Da, the term oligomer is used for molecules with a molecular weight of approximately 1000 to approximately 10,000 Da whereas the term polymer refers to molecules with a molecular weight of approximately 10,000 Da or more.

In one embodiment of the invention, the supporting monomer, oligomer or polymer has a molecular weight in the range of about 500 to about 100,000, and preferably is an oligomer with a molecular weight in the range of about 1,000 to about 10,000. Particularly good results were obtained with a supporting oligomer in the range of about 2,000 to about 6,000. The number of reactive groups per molecule of the supporting monomer, oligomer or polymer is preferably in the range of about 1.2 to about 64, more preferably in the range of about 1.2 to about 16, most preferably in the range of about 1.2 to about 8.

The functional oligomer or polymer is capable of providing a function to a coating, such as for instance, but not limited to lubricity, hydrophilicity, hydrophobicity, imageability or drug eluting capacity. The functional oligomer or polymer may be synthetic or bio-derived and can be blends or copolymers of both. The synthetic hydrophilic polymers include but are not limited to poly (lactams) eg PVP or PVC, homo and copolymers of acrylic and methacrylic acid, polyvinyl alcohol, polyvinylethers, maleic anhydride based copolymers, polyesters, vinylamines, polyethyleneimines, polyethyleneoxides, poly(carboxylic acids), polyamides, polyanhydrides and polyphosphazenes. The bioderived or bio-inspired hydrophilic polymers include but are not limited to cellulosics (carboxymethyl cellulose, methyl, hydroxyethyl or hydroxypropyl), heparin, dextran, chondroitin sulphate, polypeptides (collagens, fibrins, elastin), polysachamides (chitosan, hyaluronic acid, alginates, gelatin, chitin, polyesters (polylactides, polyglycolides, polycaprolactones), polypeptides like collagen, albumin, oligo peptides, polypeptides, short chain peptides, proteins or oligonucleotides.

In one embodiment of the invention, the functional oligomer or polymer has a molecular weight in the range of about 8,000 to about 5,000,000, and preferably is a polymer with a molecular weight in the range of about 20,000 to about 2,000,000 and more preferably in the range of about 200,000 to about 1,300,000.

The functional oligomer or polymer should obviously be used in more than 0% of the coating composition, preferably more than 1 such as 2%. The functional oligomer or polymer can be present in the coating composition up to 90%, however, more often the functional oligomer or polymer will be used up to 50, 60, 70 or 80%. A typical range for the content of the functional oligomer or polymer in the coating solution is 1-20%.

The ratio of functional oligomer or polymer to supporting monomer, oligomer or polymer may for example vary between 10:90 and 90:10, such as between 25:75 and 75:25 or such as between 60:40 and 40:60. The examples section shows examples of particularly advantageous coating compositions wherein the said ratio is 50:50.

A suitable photoinitiator for use in the invention is a compound capable of performing a photochemical Norrish type I cleavage reaction or other photochemical homolytic bond cleavage. Photoinitiated polymerisation can be initiated by two types of photoinitiators. Norrish Type I photoinitiators, which occur by homolytic cleavage of the chromophore directly to generate radicals that initiate polymerization and Norrish Type II photoinitiators that generate radicals indirectly by hydrogen abstraction from a suitable synergist eg tertiary amine. More in detail: free-radical photoinitiators are generally divided into two classes according to the process by which the initiating radicals are formed. Compounds that undergo unimolecular bond cleavage upon irradiation are termed Norrish Type I or homolytic photoinitiators, as shown by formula (1):

(1)

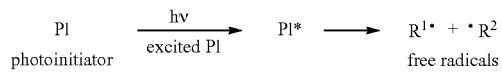

Depending on the nature of the functional group and its location in the molecule relative to the carbonyl group, the fragmentation can take place at a bond adjacent to the carbonyl group ($\alpha$-cleavage), at a bond in the $\beta$-position ($\beta$-cleavage) or, in the case of particularly weak bonds (like C—S bonds or O—O bonds), elsewhere at a remote position. The most important fragmentation in photoinitiator molecules is the $\alpha$-cleavage of the carbon-carbon bond between the carbonyl group and the alkyl residue in alkyl aryl ketones, which is known as the Norrish Type I reaction.

If the excited state photoinitiator interacts with a second molecule (a coinitiator COI) to generate radicals in a bimolecular reaction as shown by formula (2), the initiating system is termed a Type II photoinitiator. In general, the two main reaction pathways for Type II photoinitiators are hydrogen abstraction by the excited initiator or photoinduced electron transfer, followed by fragmentation. Bimolecular hydrogen abstraction is a typical reaction of diaryl ketones. Photoinduced electron transfer is a more general process, which is not limited to a certain class of compounds.

(2)

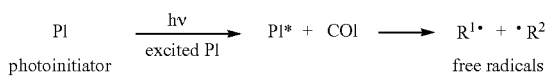

Examples of suitable Type I or cleavage free-radical photoinitiators are benzoin derivatives, methylolbenzoin and 4-benzoyl-1,3-dioxolane derivatives, benzilketals, $\alpha,\alpha$-dialkoxyacetophenones, $\alpha$-hydroxy alkylphenones, $\alpha$-aminoalkylphenones, acylphosphine oxides, bisacylphosphine oxides, acylphosphine sulphides, halogenated acetophenone derivatives, and the like. Commercial examples of suitable Type I photoinitiators are Irgacure 2959 (2-hydroxy-4'-(2-hydroxyethoxy)-2-methyl propiophenone), Irgacure 651 (benzildimethyl ketal or 2,2-dimethoxy-1,2-diphenylethanone, Ciba-Geigy), Irgacure 184 (1-hydroxy-cyclohexyl-phenyl ketone as the active component, Ciba-Geigy), Darocur 1173 (2-hydroxy-2-methyl-1-phenylpropan-1-one as the active component, Ciba-Geigy), Irgacure 907 (2-methyl-1-[4-(methylthio)phenyl]-2-morpholino propan-1-one, Ciba-Geigy), Irgacure 369 (2-benzyl-2-dimethylamino-1-(4-morpholinophenyl)-butan-1-one as the active component, Ciba-Geigy), Esacure KIP 150 (poly{2-hydroxy-2-methyl-1-[4-(1-methylvinyl)phenyl]propan-1-one}, Fratelli Lamberti), Esacure KIP 100 F (blend of poly{2-hydroxy-2-methyl-1-[4-(1-methylvinyl)phenyl]propan-1-one} and 2-hydroxy-2-methyl-1-phenyl-propan-1-one, Fratelli Lamberti), Esacure KTO 46 (blend of poly {2-hydroxy-2-methyl-1-[4-(1-methylvinyl)phenyl]propan-1-one}, 2,4,6-trimethylbenzoyldiphenyl-phosphine oxide and methylbenzophenone derivatives, Fratelli Lamberti), acylphosphine oxides such as Lucirin TPO (2,4,6-trimethylbenzoyl diphenyl phosphine oxide, BASF), Irgacure 819 (bis (2,4,6-trimethylbenzoyl)-phenyl-phosphine-oxide, Ciba-Geigy), Irgacure 1700 (25:75% blend of bis(2,6-dimethoxybenzoyl)2,4,4-trimethyl-pentyl phosphine oxide and 2-hydroxy-2-methyl-1-phenyl-propan-1-one, Ciba-Geigy), and the like. Also mixtures of type I photoinitiators can be used. For colored (e.g. pigmented) systems, phosphine oxide type photoinitiators and Irgacure 907 are preferred.

Photoinitiators may be used in the conventional way, this means that a skilled person will be aware of the amount of photoinitiator required to obtain a desired effect. In general, an amount of more than 0 to 10%, such as 0.2 to 5% will be sufficient for most purposes.

The term solvent is used herein in its normal sense. Any solvent can in principle be used in the present invention. Preferred solvents include 1,3-dioxolane and other ethers, acetone and other ketones, dimethyl sulfoxide and other sulfoxides, dimethyl formamide and other amides, N-methyl-2-pyrrolidone and other lactams, ethanol and other alcohols, glycols, glycol ethers, glycol esters, other esters, amines, heterocyclic compounds, morpholine and derivatives, alkylated urea derivatives, liquid nitriles, nitroalkanes, haloalkanes, haloarenes, trialkyl phosphates, dialkyl alkanephosphonates, and other commonly known organic solvents. The preferred solvents may either be used singly or in combination. Currently preferred solvents are selected from water, alcohols such as ethanol, N-methyl-2-pyrrolidone, dimethyl sulfoxide, acetone, 1,3-dioxolane and dimethyl formamide.

The solvent is preferably a volatile or fairly volatile solvent. The terms "volatile solvent" and "fairly volatile solvent" should be seen in the light of the evaporation rate. For this purpose, the evaporation rate relative to butyl acetate is typically used to provide certain guidelines in this respect (see in particular A. Saarnak, C. M. Hansen:"Loslighedsparametrar, Karaktarisering avfärgbindemedel och polymerer", publication from the Scandinavian Paint and Printing Ink Research Institute, Hrsholm, Denmark, May 1982 (in Swedish)). According to this paper, the evaporation rate (ER) is "Fast" if it is more than 3.0 times greater than that of butyl acetate (ER=1.0), i.e. ER>3.0; "Medium" if 0.8<ER<3.0; "Slow" if 0.1<ER<0.8; and "Very slow" if ER<0.1. "Volatile" and "Fairly volatile" correspond to "fast" and "medium" evaporation rate, respectively.

The supporting monomer, oligomer or polymer may be mixed with the other ingredients into a coating composition in any manner known in the art and applied to the surface. Any wet coating application method may be suited for this purpose. These include but are not limited to methods known in the art as dip coating, die coating, spray coating, curtain coating or transfer coating. The thickness of the coating may vary between more than 0 and 1 cm, preferably, the coating composition is applied in a thickness that results in a dry coating of more than 0 to 100 micrometers.

The supporting monomer, oligomer or polymer is then cross-linked by exposure to a suitable energy source. This energy source may for instance be selected from the group consisting of light, such as UV, visible or near IR, microwave, electron beam or plasma. The goal of exposing the coating composition to the energy source is of course the effective cross-linking of the supporting monomer, oligomer or polymer. What effective means in this respect is to some extent determined by the desired function of the coating In most if not all instances the first exposure to the energy source should be sufficient to cause the formation of a network of the supporting monomer, oligomer or polymer beyond its gelpoint. Usually, this means that the conversion of the functional moieties attached to the supporting monomer, oligomer or polymer is more than 40%, such as more than 60%, 70%, 80% or 90%, preferably, however, more than 95%. Conversion of the functional moieties attached to the supporting monomer, oligomer or polymer may be determined by any suitable method available in the prior art, one suitable method is exemplified hereinafter in the Examples section.

It is preferred to use an artificial energy source (i.e. not a natural source like sunlight) capable of delivering a dose of energy so that the desired level of cross-linking of the supporting monomer, oligomer or polymer is achieved within a reasonable amount of time, such as less than 10 minutes, such as less than 7, 6, 5, 4 or even 3 minutes. For high-throughput applications it may be desired to use an energy source capable of delivering a high dose in a minimal amount of time, even in the order of seconds. It is anticipated that best results are obtained when an energy source is used capable of delivering a total dose in the order of 10 mJ/cm$^2$ to 50 J/cm$^2$, preferably in the order of 2-10 J/cm$^2$.

After being exposed to the energy source, the coating is then subjected to an evaporation step. This may for instance conveniently be accomplished by a simple heat treatment, using radiative or conductive sources or an air current or exposure to another inert gas, such as N2, Ar, or CO2. Applying a reduced pressure or vacuum may facilitate the speed of the evaporation step. Other methods of evaporating the solvent are feasible as well.

Yet another exposure to the energy source is required to obtain the full benefit of the invention, i.e. the functional oligomer or polymer becomes more effectively grafted to the network already after a second exposure. For practical reasons, it is preferred to use the same energy source and/or dose and/or exposure time as used in the first exposure, although this is not mandatory.

The procedure may be repeated again for even better results, i.e after the second exposure to the energy source, the solvent is evaporated again and the coating is exposed to the energy source for the third or fourth or any further time. The invention therefore also relates to a process according to claim 1, wherein said step of evaporating the solvent is repeated after the last exposure of the coating composition to the energy source.

Figure 8:
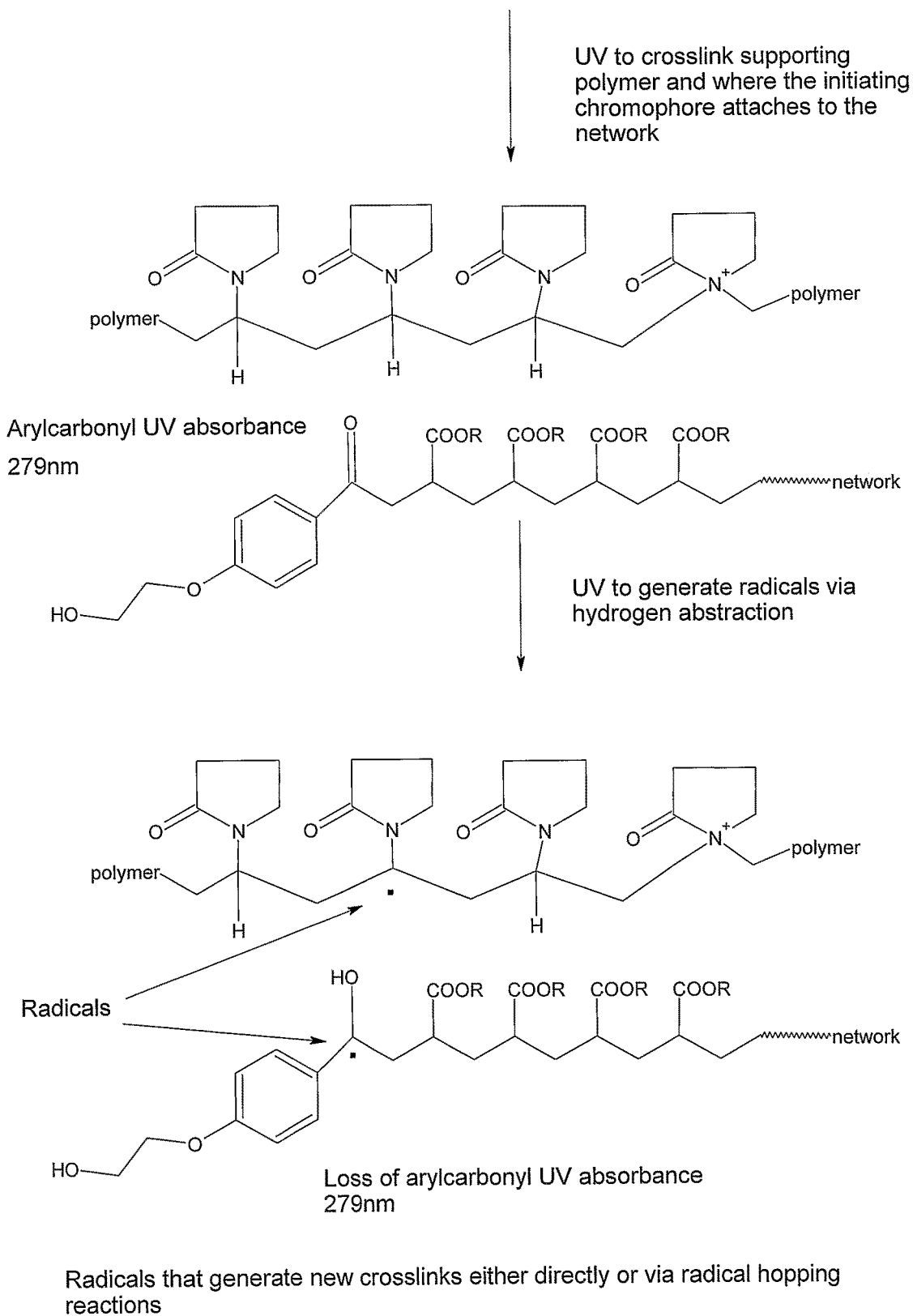

We estimate (without wanting to be bound by theory) that the observed improvement in grafting of the functional oligomer or polymer is accomplished through a dual use of the Norrish type I photoinitiator (FIG. 1), firstly to initiate polymerisation of the supporting monomer, oligomer or polymer forming the network in a Norrish type I photoinitiation reaction, and secondly to generate extra cross-links with the functional oligomer or polymers by hydrogen abstraction reaction via the chromophore that is bound to the supporting monomer, oligomer or polymer via the initiation of polymerisation. This hydrogen abstraction reaction results in the formation of new radicals both on the supporting monomer, oligomer or polymer and the functional oligomer or polymer. These radicals can react to form new crosslinks either directly or indirectly. This is represented schematically in FIG. 8.

Optionally, biologically active compounds like drugs or peptides may be added to the coating in any way convenient for the application. Such procedures are known in the art. In case a coating is used for imaging or antimicrobial purposes, fillers may be added, such as silver, platinum, BaSO4, silica, titania zirconia, core shell rubber, pigments or coloring agents. Encapsulants like micelles, liposomes, polymerosomes, dendrimers, yeast cell walls and the like may be used to encapsulate molecules to be dispersed into a coating.

Conventional coatings may be revalued by the above-described invention. It may be clear now that functional oligomers or polymers may be better grafted onto a supporting network formed from a supporting monomer, oligomer or polymer by applying a sequential cross-linking and evaporation step as described in the invention above. This appeared to be true for a wide range of applications. The examples below describe coatings with improved functional properties including hydrophilicity, lubricity, anti-microbial, anti-thrombogenic, and imaging function, anti-calcifying agents, fungicidal, wear resistance and hydrophobicity.

The invention also relates to a cross-linked functional coating, wherein a supporting monomer, oligomer or polymer capable of forming a supporting network is covalently attached to at least one functional oligomer or polymer through a Norrish type I or homolytic bond cleavage photopolymerisation reaction.

A coating according to the present invention has also excellent properties with respect to its wear resistance. Cross-linked functional coatings according to the prior art showed large variations in their ratio of static to dynamic friction when tested in the wear resistance test as described herein below, whereas coatings according to the invention showed essentially the same ratio of static to dynamic friction over a test period of 53 cycles.

In all the below examples a better grafting of the functional oligomer or polymer was obtained without compromising the functional properties of the coating. Moreover, in some instances the functional properties of the coating were even improved in comparison to conventional coatings, on top of the fact that the functional oligomer or polymer was better grafted in the coating. The invention therefore relates to a coating obtainable by the processes as described above.

The invention therefore relates to a method for obtaining a cross-linked functional coating, such as for instance a hydrophilic coating or a lubricious coating wherein a polymer solution is used comprising
- at least one supporting monomer, oligomer or polymer capable of forming a supporting network
- at least one functional oligomer or polymer
- at least one photoinitiator capable of performing a Norrish type I or homolytic bond cleavage photopolymerisation reaction As exemplified, these coatings are particularly advantageous when applied on a medical device. The invention therefore also relates to a medical device comprising a coating according to the invention.

Figure 5:
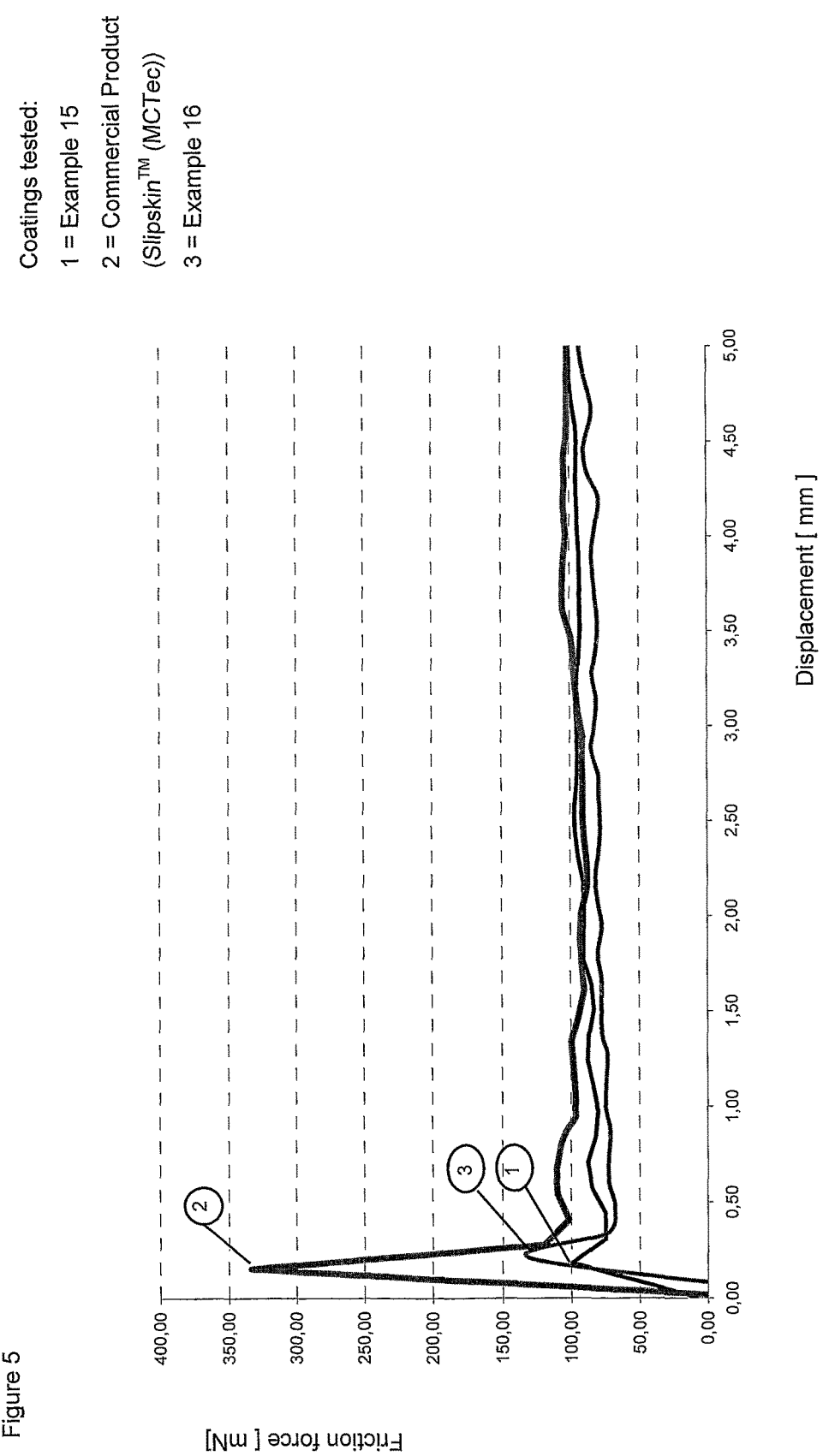

One important property of coils comprising a lubricious coating is that they should exhibit an as low as possible static friction force. Another important parameter is that such a coil should have a constant dynamic friction force over the time of use of the coil. With such a coil, the user (mostly a surgeon) can predict the amount of force necessary for the coil to move in the patient's body, otherwise the use of the coil could lead to serious injuries for the patient. The data obtained with the coils coated according to the invention fulfilled both requirements; i.e. they have a constant dynamic friction over time whereas they have virtually no static friction as evidenced by a long-lasting ratio of static friction over dynamic friction of 1 or close to 1 (FIG. 5).

As described in examples 16 and 17, the performance of the coils according to the invention appeared to be more constant over time of use than the prior art devices. The large variation in the ratio's obtained with the commercial samples appears mainly due to a large cycle to cycle variation of their static friction, whereas their dynamic friction was relatively 'constant' from cycle to cycle, which means, however, that their dynamic friction still roughly doubled over the course of the experiment. In contrast, the static as well as dynamic friction values obtained with the coatings according to the invention were both remarkably constant. From these data it is obvious that the coefficient of variation of the ratio static/dynamic friction of a coating according to the invention is well below 9 whereas this coefficient of variation for prior art coatings is well above 17. The invention therefore relates to a coating that exhibits a coefficient of variation of the ratio static/dynamic friction of below 17, when tested in a wear resistance test as described in example 20 or in the claims hereinafter.

Figure 7:
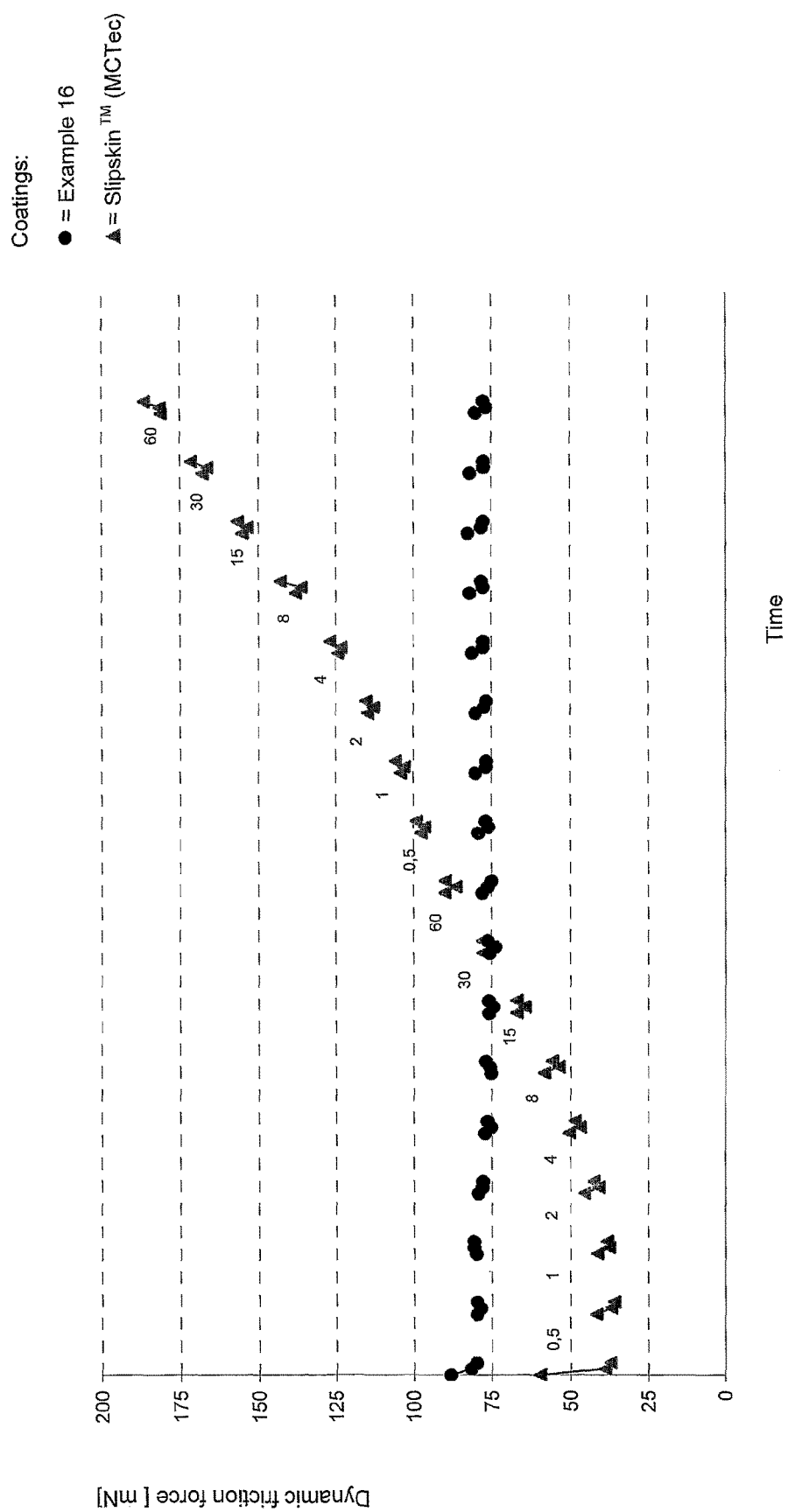

In a wear resistance test as described in example 21, it appears that a coil coated with a lubricious coating according to the invention exhibited an average dynamic friction force over 51 cycles of 78 mN (Standard deviation 2.1) whereas a coil coated with a lubricious coating according to the prior art exhibited an average dynamic friction force of 94 mN (Standard deviation 47.1). In a heavy-duty wear resistance test, it also appeared that the dynamic friction force of a coil with a coating according to the invention remained remarkably constant over time, whereas the coil with a coating according to the prior art varied 5-fold (from 36 mN to 186 mN, table 8). This is reflected by the coefficient of variation of the values obtained with the two different coils; a coil with a coating according to the invention had a coefficient of variation of 2,7%, whereas the coil with a coating according to the prior art had a coefficient of variation of 50% (FIG. 7, table 8)

The invention also relates to coatings obtainable by any of the processes as described herein above.

The invention also relates to a cross-linked polymer coating whereby the amount of migrateables is less than 10 weight %, such as less than 8%, 7% or 6%.

The invention also relates to a medical device comprising a coating according to the invention The invention also relates to a method for determining the static friction force of a coated coil comprising the steps of:
- Providing a catheter tube with an inner diameter suitable to tightly accommodate the coated coil
- Placing the catheter in a holding device such that the catheter forms a half circle with a diameter of 40 mm
- Placing the coated coil inside the catheter tube
- Immersing the catheter tube in a water bath of 23 degrees C.
- Flushing the catheter tube with water
- Attaching the coated coil to a tensiometer attached to a 20N load cell
- Moving the coated coil in a push and pull cycle within the catheter with a speed of approximately 200 mm per minute
- Measuring the static friction as the maximum force in the first 2 mm of the pull part of the cycle.

The invention also relates to a method for determining the dynamic friction force of a coated coil comprising the steps of:
- Providing a catheter tube with an inner diameter suitable to tightly accommodate the coated coil
- Placing the catheter in a holding device such that the catheter forms a half circle with a diameter of 40 mm
- Placing the coated coil inside the catheter tube
- Immersing the catheter tube in a water bath of 23 degrees C.
- Flushing the catheter tube with water
- Attaching the coated coil to a tensiometer attached to a 20N load cell
- Moving the coated coil in a push and pull cycle within the catheter with a speed of approximately 200 mm per minute
- Measuring the dynamic friction as the average force from 2 to 5 mm of displacement of the pull part of the cycle.

The invention also relates to a method for determining the ratio of static friction/dynamic friction of a coated coil comprising the steps of:

Providing a catheter tube with an inner diameter suitable to tightly accommodate the coated coil Placing the catheter in a holding device such that the catheter forms a half circle with a diameter of 40 mm Placing the coated coil inside the catheter tube Immersing the catheter tube in a water bath of 23 degrees C.

Flushing the catheter tube with water

Attaching the coated coil to a tensiometer attached to a 20N load cell

Moving the coated coil in a push and pull cycle within the catheter with a speed of approximately 200 mm per minute Measuring the static friction as the maximum force in the first 2 mm of the pull part of the cycle, Measuring the dynamic friction as the average force from 2 to 5 mm of displacement of the pull part of the cycle Dividing the static friction force by the dynamic friction force.

The invention also relates to a coated coil comprising a lubricious coating comprising a cross-linked polymer said coil having a static friction force of less than 300, preferably less than 200, such as 175 or 150 as measured in the method described above.

The invention also relates to a coated coil comprising a lubricious coating comprising a cross-linked polymer said coil having a ratio of static friction/dynamic friction after 4 initial cycles of less than 2, as measured in the method as described above.

The invention also relates to a coated coil comprising a lubricious coating comprising a cross-linked polymer, said coil having a average ratio of static friction/dynamic friction of less than 2.9, preferably less than 2.5, such as less than 2.2, 2.0, 1.8, 1.7, 1.6, or 1.5 wherein said average ratio is determined over the first 52 or 53 measurements of ratios of static friction/dynamic friction as measured in the method as described above.

The invention also relates to a coated coil comprising a lubricious coating comprising a cross-linked polymer, said coil having a coefficient of variation of less than 15% preferably less than 12%, such as 11, 10 or 9% between the ratios of static/dynamic friction measured over the first 52 or 53 cycles as measured in the method as described above.

The invention also relates to a coated coil comprising a lubricious coating comprising a cross-linked polymer said coil having a coefficient of variation in the friction force of less than 50%, preferably less than 45% such as 40%, 30%, 20%, 10%, 8%, 6%, 4%, or even 3%, wherein said coefficient of variation is determined over the ratios of static/dynamic friction measured over the first 51 cycles as measured in the method described above.

FIGURE LEGENDS

FIG. 1: Schematic representation of the dual use of a Norrish type I photoinitiator; first for cross-linking and second for grafting of a non cross-linking polymer.

Figure 2:
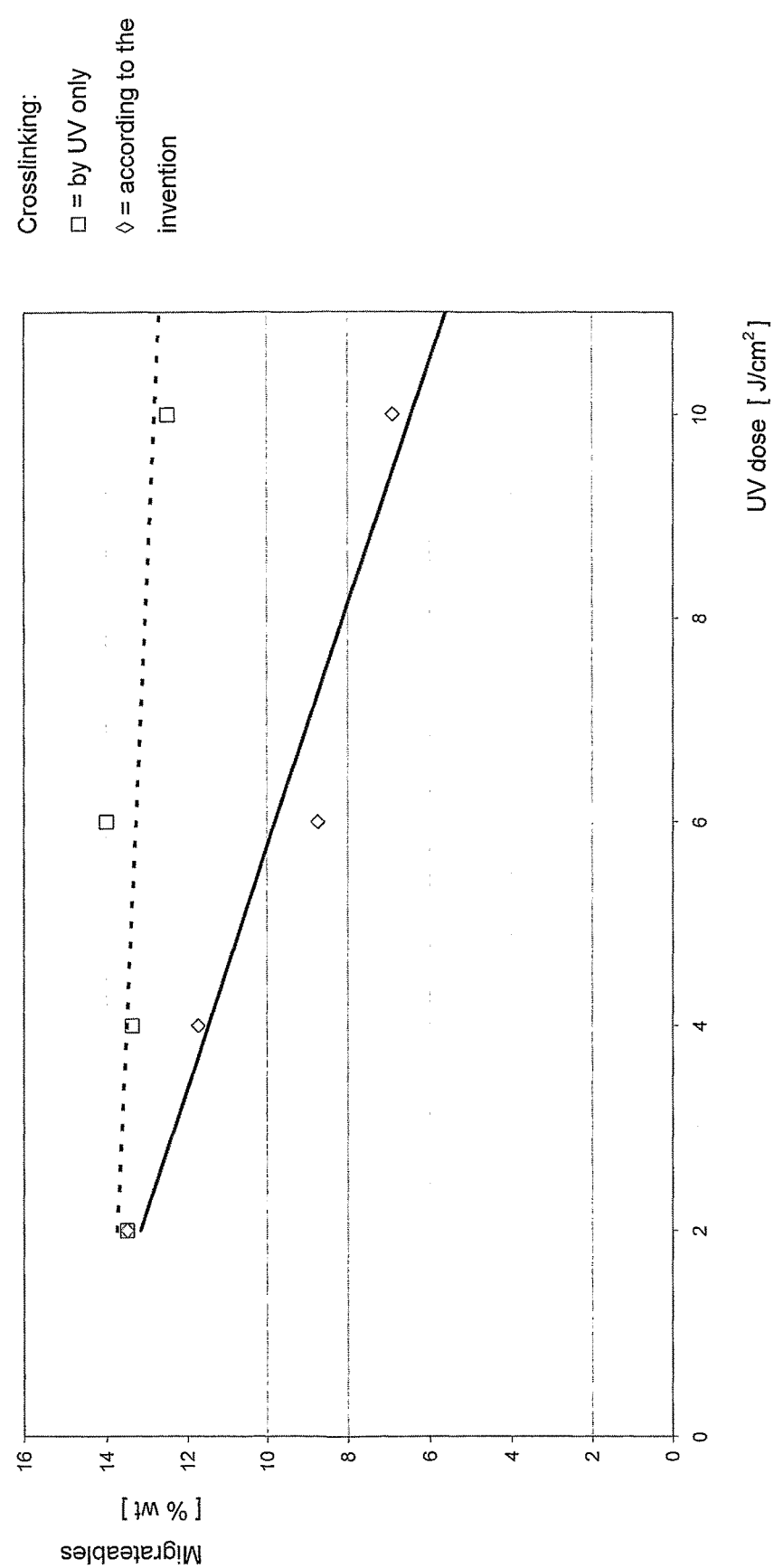

FIG. 2. Graph representing the amount of migrateables that can be extracted from a coating according to the prior art treated with UV only (squares) and from a coating prepared by a method according to the invention (diamonds). Y-axis: amount of migrateables in weight percentages extracted, X-axis: UV dose in J/cm$^2$.

Figure 3:
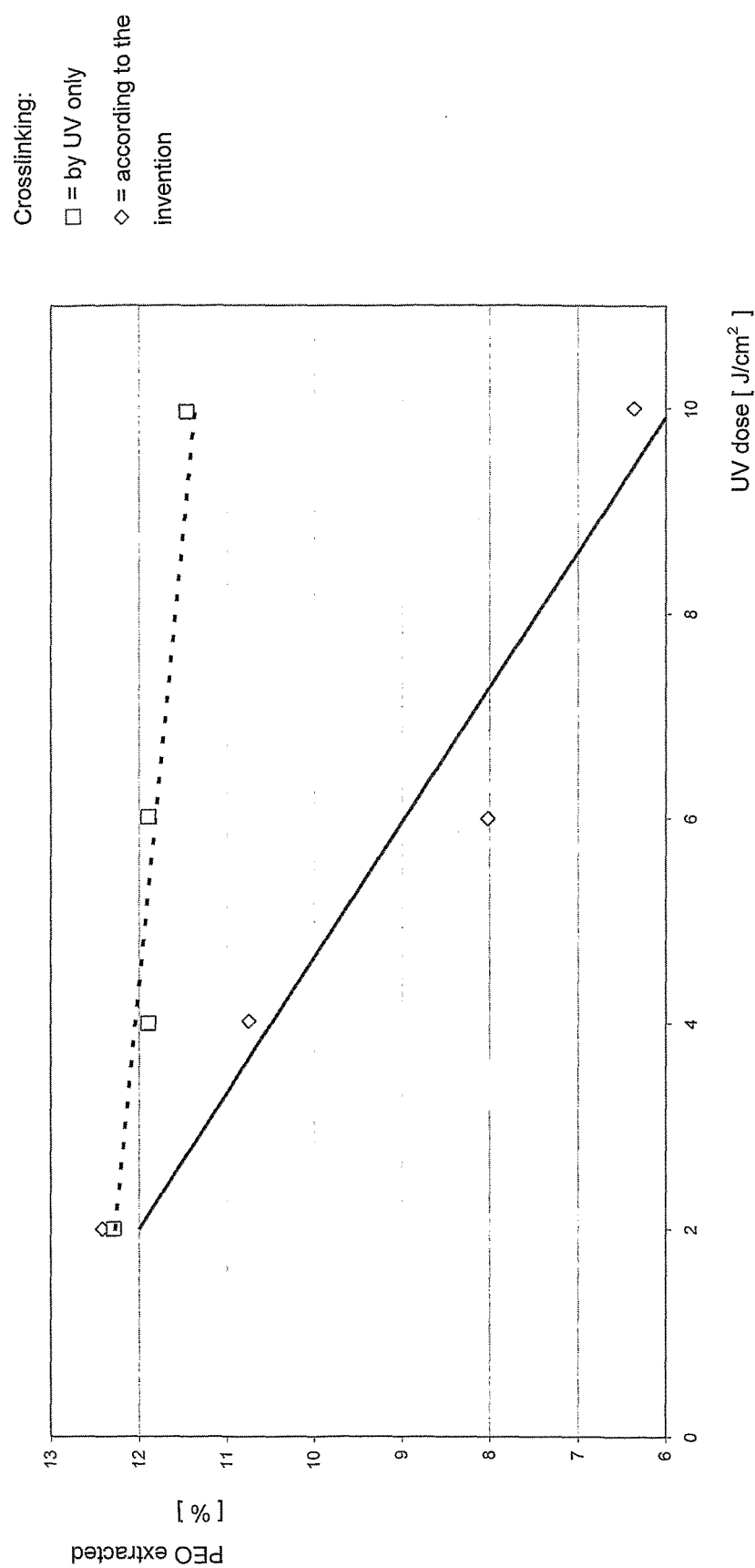

FIG. 3 Graph representing the amount of PEO that can be extracted from a coating according to the prior art treated with UV only (squares) and from a coating prepared by a method according to the invention (diamonds). Y-axis: percentage PEO extracted, X-axis: UV dose in J/cm$^2$.

Figure 4:
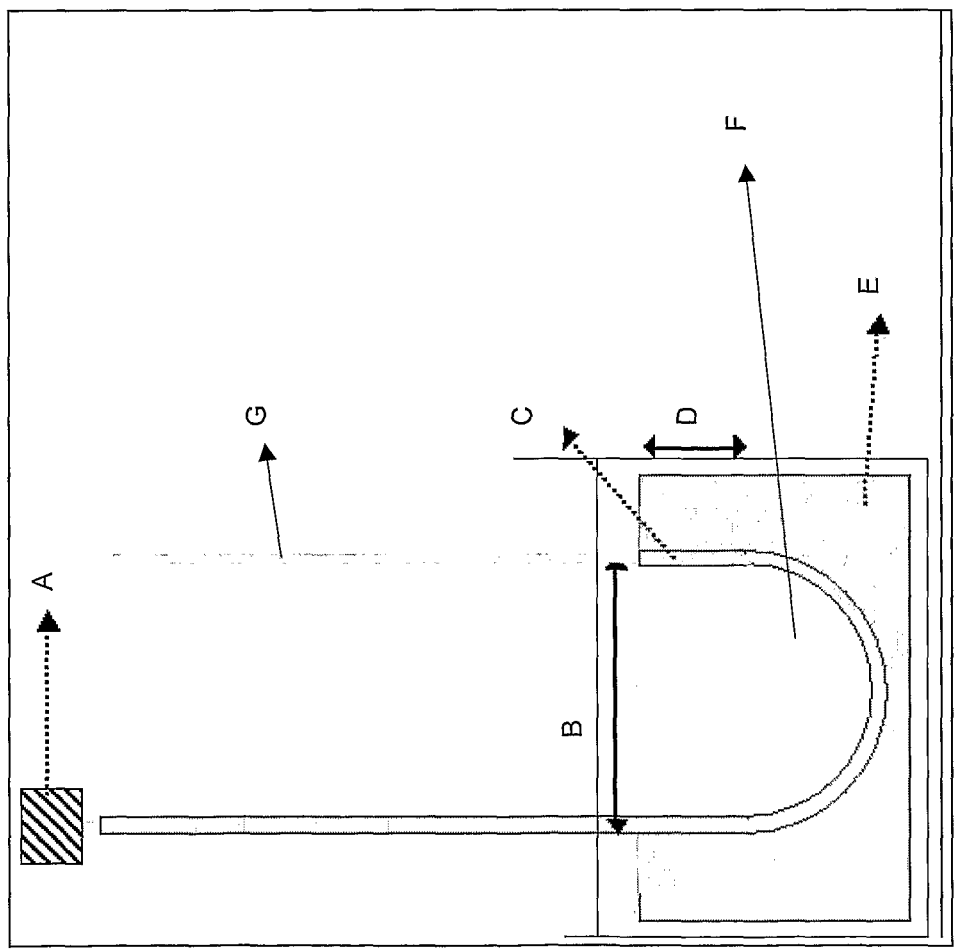

FIG. 4: Schematic illustration of the wear resistance test described in example 18. A: clamp to the tensiometer load cell, B: distance of 40 mm, C: catheter tube (filled with water), D: distance of 15 mm, E: support mold, F: water, G: coated coil.

FIG. 5: Comparison of the lubricity of coated coils from Examples 15 (1) and 16 (3), against a commercial product CP (2). The static friction of both coatings according to the invention is remarkably lower than the static friction of a commercial sample, whereas the dynamic frictions are essentially the same. Y-axis=friction force (mN), X-axis=displacement (mm).

Figure 6:
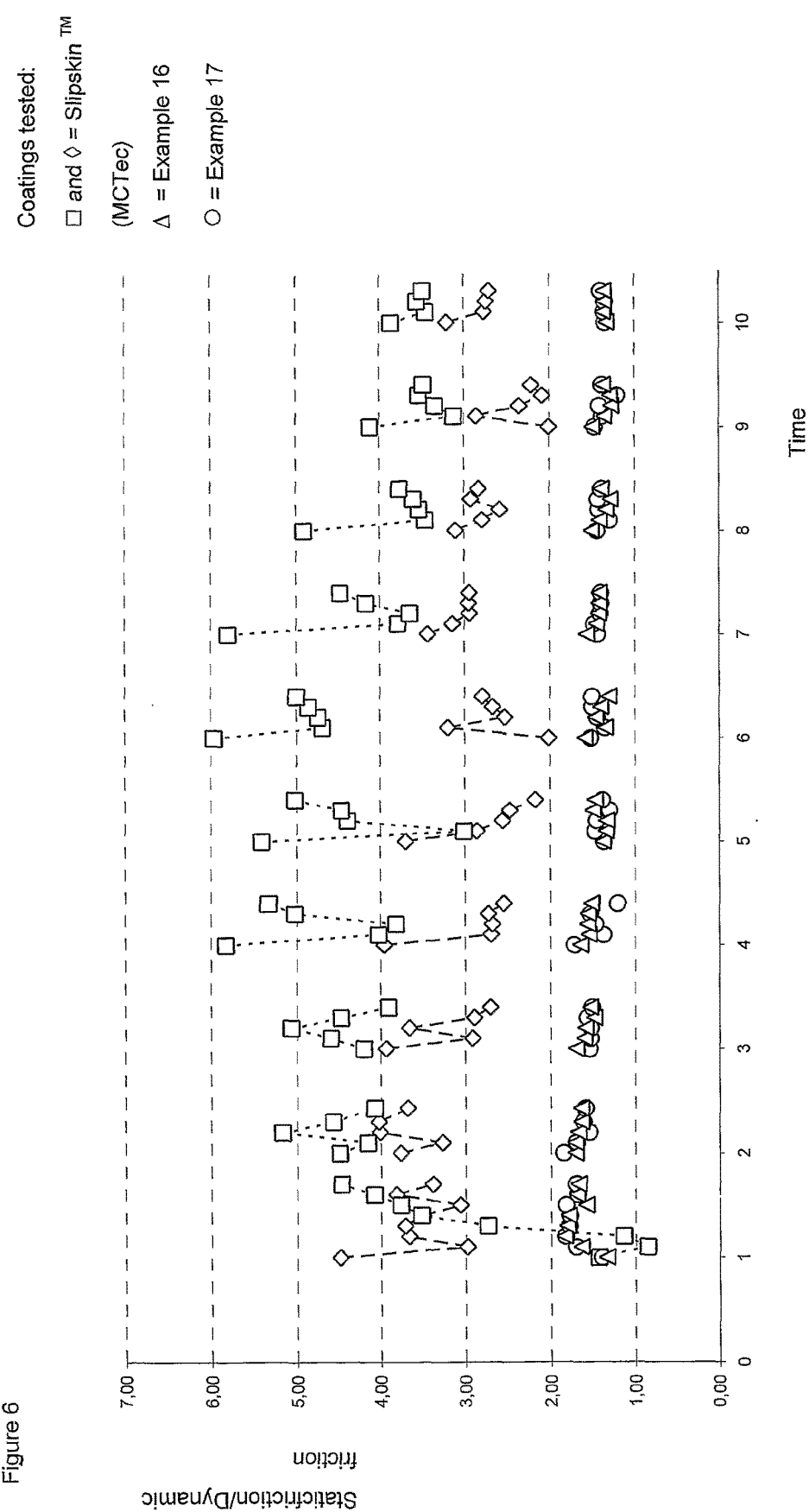

FIG. 6: Comparison of the wear resistance of coated coils from Example 16 (triangles) and 17 (circles) against two specimens of a commercial product CP (squares and diamonds).

Y-axis=Static friction/dynamic friction, X-axis=non-linear time scale. Each data point represents the ratio static friction/dynamic friction averaged from 2 to 5 mm of displacement in a single cycle. After the first 8 cycles, nine series of 5 cycles each were performed with a waiting time of 15 minutes in between each series.

FIG. 7: Changes in dynamic friction force over time-of-use. This graph shows how the dynamic friction forces change over time when 3 cycles of friction measurement were performed followed by varying waiting times as indicated in the graph. For instance, the first triplet of cycles was followed by a waiting time of 0.5 minutes before the second triplet of cycles were performed which was then followed by a waiting time of 1 minute before again the next triplet of cycles was performed. Circles: coil coated with a coating according to example 16, triangles: data obtained with a commercial product CP FIG. 8: Proposed mechanism of photografting reaction.

Figure 9:
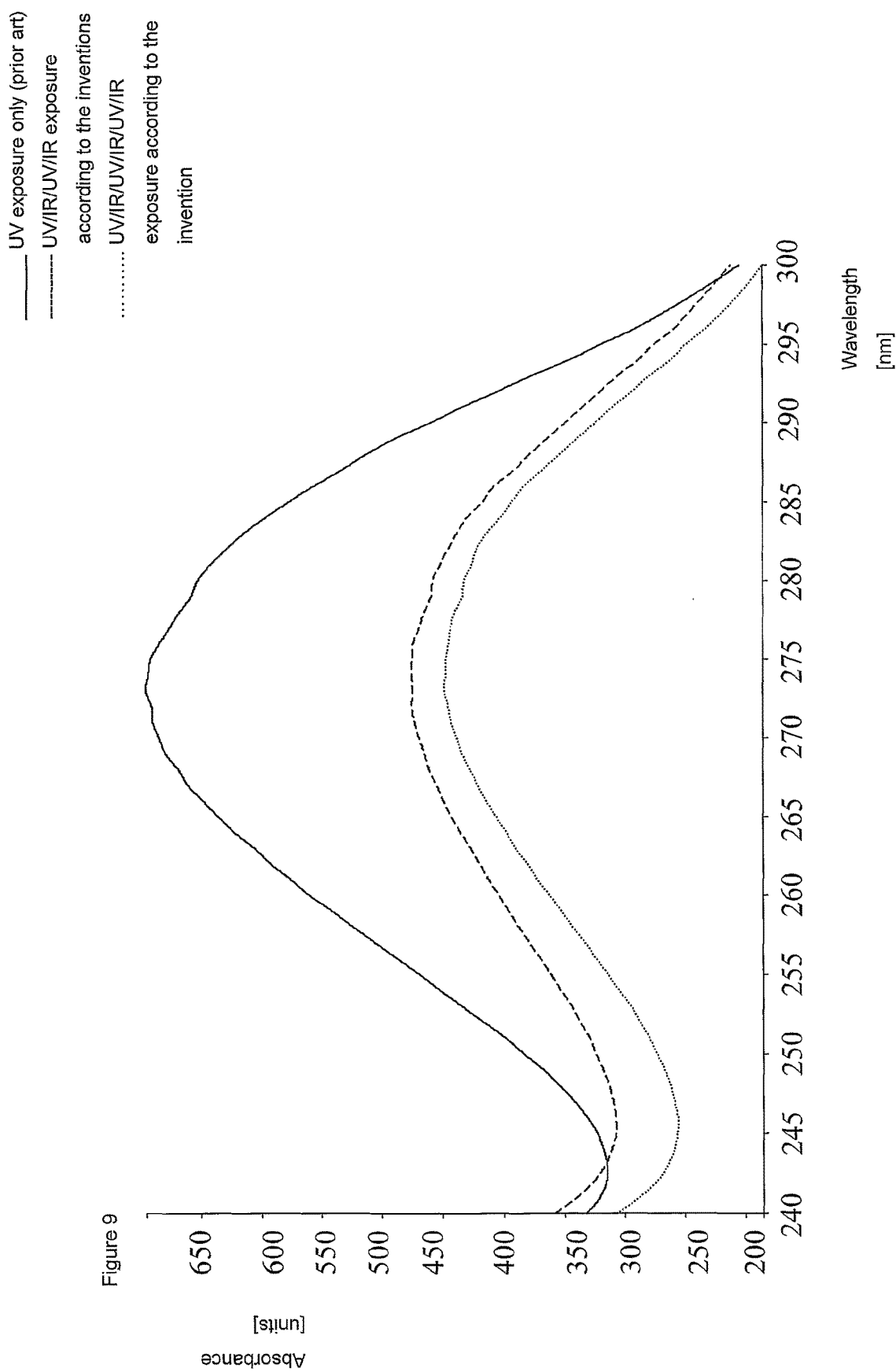

FIG. 9: Diagram showing the absorbtion profiles of a coating according to the prior art (continuous line, UV exposure only), a coating according to the invention (dashed line, UV/IR/UV/IR) and another coating according to the invention (dotted line UV/IR/UV/IR/UV/IR). This graph clearly shows that the arylcarbonyl chromophore is consumed in the process of solvent evaporation followed by UV exposure. X-axis: wavelength (nm), Y-axis: arbitrary absorbance units.

Figure 10:
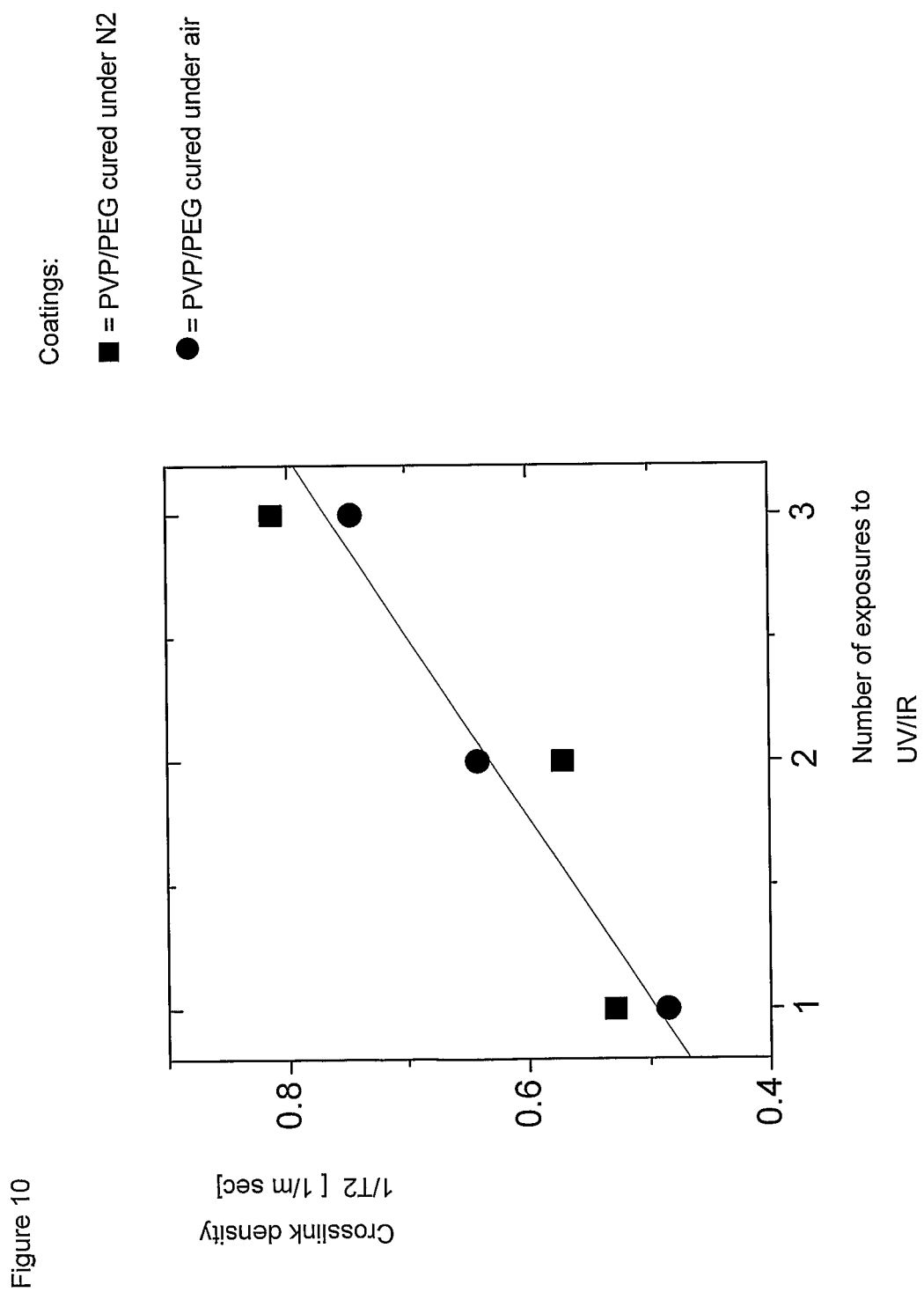

FIG. 10: Graph showing the cross-link density (expressed as 1/T2) against number of UV exposures separated by evaporation of the solvent. The figure clearly shows an increase in cross-link density with each addition UV exposure. Y-axis: The rate of proton $T_2$ relaxation, $1/T_2$ (in ms$^{-1}$), X-axis: number of exposures to UV separated by evaporation of the solvent (one, two or three UV exposures) Squares: PVP/PEG coatings cured under nitrogen atmosphere, circles PVP/PEG coatings cured under air. Thickness of coatings was 24 micrometers. The relaxation rate was measured at 70° C. The line shows a least-squares fit of the data (Y=a+bX), where a=0.36±0.05; b=0.14±0.02, the correlation coefficient is 0.95, the standard deviation is 0.05.

Figure 11:
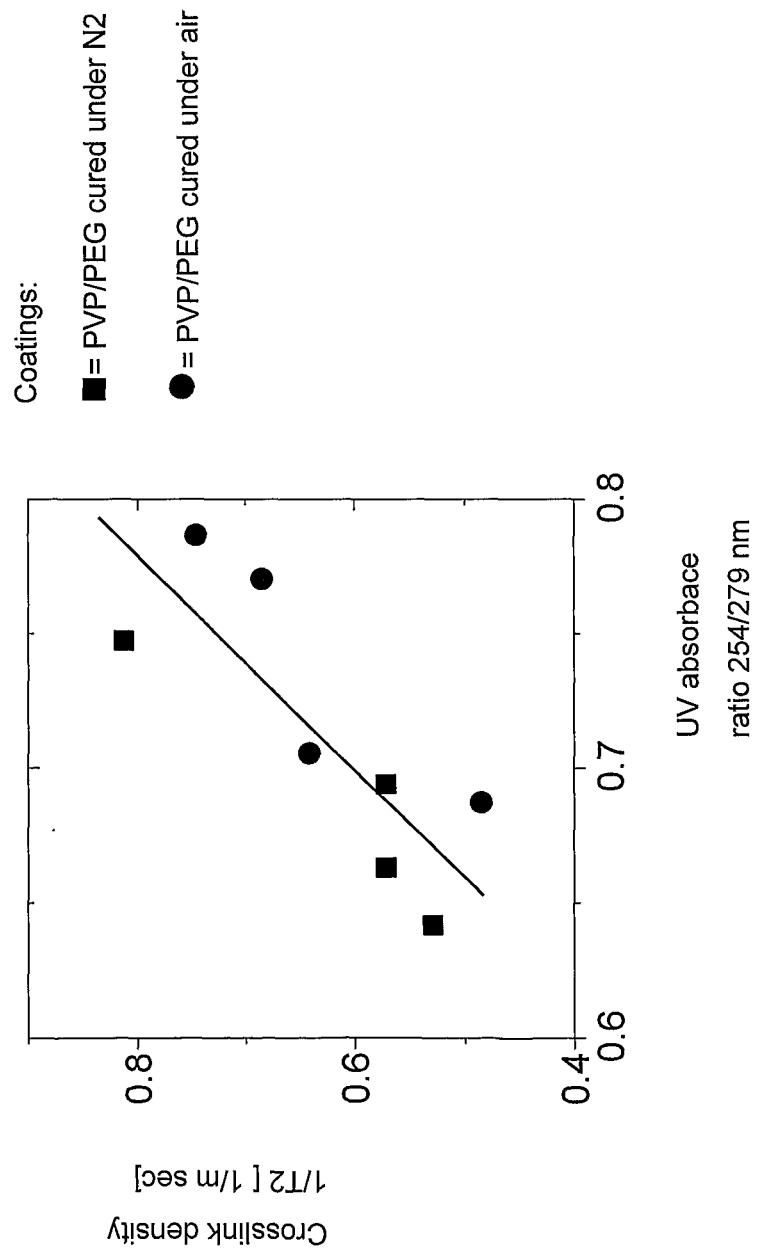

FIG. 11 Relationship between the crosslink density (expressed as 1/T2) shown by proton T2 relaxation experiments and consumption of the arylcarbonyl chromophore.

Y-axis: The rate of proton $T_2$ relaxation, $1/T_2$ (in ms$^{-1}$), X-axis: UV absorbance ratio 254 nm/279 nm. Squares: PVP/PEG coatings cured under nitrogen atmosphere, circles: PVP/PEG coatings cured under air. Thickness of coatings was 24 micrometers. The relaxation rate was measured at 70° C. The graph clearly shows that the cross-link density (expressed as 1/T2) increases with increasing ratio of UV-absorbances (254 nm/279 nm).

EXAMPLES

Example 1

Synthesis of PEG4000 Diacrylate Supporting Oligomer 150 grams of PEG 4000 diol (Biochemika Ultra from Fluka) [95904], OH-value: 28.02 mg KOH/g, 499.5 meq/kg,) was dissolved at 45° C. in 450 ml of dry toluene under nitrogen. The PEG/toluene solution was dried by azeotropic distillation at 50° C./70 mbar. Acryloyl chloride (8.15 grams, 90 mmol) and triethylamine (9.10 grams, 90 mmol) were both diluted with 50 ml dry toluene and added dropwise to the PEG diol-toluene solution. The reaction was stirred under nitrogen at 45-50° C. for at least 4 hours. To ensure a complete acrylate end capping an additional 10 mmol of acryloyl chloride and triethylamine was added to the reaction mixture allowing it to react for 1 hour. The reaction mixture was filtered warm to remove the Et3NHCl salt. Approximately 300 ml of toluene was removed under vacuum (50° C., 20 mbar). The remaining solution was kept at 45° C. in a heated dropping funnel and added dropwise to 1 liter diethyl ether cooled in an ice bath. The PEG diacrylate precipitated as white crystals. The ether solution was cooled for 1 hour before the PEG diacrylate product is obtained by a filtration. The product was dried overnight under reduced air atmosphere (300 mbar, air-flow). This procedure gave 129 g of acrylated oligomer (82% unoptimised yield).

Example 2

Synthesis of PEG2000 Diacrylate Supporting Oligomer 150 grams PEG (148 mmol OH, OH-value: 55.26 mg KOH/g, 985 meq/kg, Mn: 2030) was reacted with acryloyl-chloride (14.8 grams, 163 mmol≈1.1 eq with respect to the hydroxy groups) and triethylamine (16.6 grams, 164 mmol) according to the procedure described in Example 1 This procedure gave128 g of acrylated oligomer (83% unoptimised yield).

Example 3

Coating Composition for Extraction Studies

TABLE 1

| Materials | % w/w |
|---|---|
| PEG4000 diacrylate (PEGDA) | 17.64 |
| Polyethylene oxide, Mw~200,000 (PEO) | 1.96 |
| 2-Hydroxy-4'-(2-hydroxyethoxy)-2-methylpropiophenone (Irgacure 2959) | 0.4 |
| Distilled water | 40.0 |
| Ethanol | 40.0 |
| Total | 100.0 |

The materials were mixed together to obtain a coating composition.

Example 4

Application of Coatings for Extraction Studies

The coating composition according to Example 3 was applied onto ethanol cleaned Melinex PET sheets using a 200 µm gap doctor-blade. The weight of the PET sheets (100×150×0.125 mm) was determined prior to use with an accuracy of 0.1 mg. Directly after application of the coating composition onto the PET sheet, the coating composition was exposed to UV-light (Fusion F600 D-bulb with a UV dose of 2 J/cm$^2$. The coatings that result from this treatment are referred to as obtained with UV only.

The next series of experiments were designed to show that better grafting is obtained when, after the first UV treatment, the solvent is evaporated followed by another UV treatment. Control experiments were performed without evaporation of the solvent between the individual UV curing steps.

The IR lamps consist of six 30 cm 1000 W Philips lamps placed 5 cm apart and 10 cm above the coated sample. Heating was done for 12 seconds, during these 12 seconds, the temperature of the surface did not exceed 150° C. The procedure of UV irradiation and evaporation was repeated such that coatings were obtained that were exposed to consecutive cycles of UV and evaporation between 1 and 4 times after the first UV treatment (table 2).

TABLE 2

| Condition | Corresponding total UV-dose |
|---|---|
| UV only | 2 J/cm$^2$ |
| UV/IR/UV/IR | 4 J/cm$^2$ |
| UV/IR/UV/IR/UV/IR | 6 J/cm$^2$ |
| UV/IR/UV/IR/UV/IR/UV/IR/UV/IR | 10 J/cm$^2$ |
| Controls | |
| UV only | 2 J/cm$^2$ |
| UV only | 4 J/cm$^2$ |
| UV only | 6 J/cm$^2$ |
| UV only | 10 J/cm$^2$ |

The coatings were then allowed to dry for 12 hours at 105° C. under reduced nitrogen atmosphere (200 mbar). After drying, a coating of approximately 40 µm in thickness was obtained. The extent of acrylate conversion was measured by ATR-FTIR. These measurements showed that the acrylate conversion was already more than 95%±2 for the single step UV only (2 J/cm$^2$) cured coatings.

For this measurement a Perkin Elmer Spectrum One FTIR spectrometer equipped with a Golden Gate attenuated total reflection (ATR) accessory was used. The spectrometer consists of a DTGS detector and the Golden Gate accessory makes use of a single bounce diamond crystal. Infrared spectra between 4000 and 650 cm$^{-1}$ were recorded averaging 32 scans with a spectral resolution of 4 cm$^{-1}$. The Spectrum for Windows software version 3.02.01 was used. Acrylate group conversions were measured by comparing the acrylate specific C—H def band at 1410 cm$^{-1}$ in the FT-IR spectra of the un-extracted UV cured coatings against the spectrum of the uncured formulation.

Example 5

Determination of Migrateables by Gravimetric Analysis

The coated PET sheets from example 4 were extracted with 200 ml distilled water, at 37° C. for 1 hour and then dried for 12 hours at 105° C., at reduced nitrogen atmosphere (200 mbar). The PET sheets were weighed before and after extraction. Uncoated PET sheets were used as a control. It was observed that the weight loss of the control sheets was negligible (<0.1% of average coating weight loss). The weight loss attributable to the amount of migrateables in the coated sheets is shown in FIG. 2.

It is clear from the data shown in FIG. 2 that UV exposure followed by a single evaporation of the solvent (by IR) and repeated UV exposure, already significantly reduced the amount of migrateables. Repetition of this treatment was found to further reduce the amount of migrateables,

Example 6

Analysis of the Migrateable Component

In order to find out which of the components of the coating actually migrated out in the experiments described in example 5, the following experiments were designed.

Theoretically, the migrateable component can only be PEO or PEGDA (the amount of photoinitiator is negligible and cannot attribute significantly to the amount of migrateables). The below procedure measures the amount of PEGDA present in the distilled water extracts and then calculates the amount of PEO. It was found that the migrateable component was predominantly (more than about 90%) PEO, whereas the coating composition contained only about 10% PEO. In more detail, the procedure was as follows.

The distilled water extracts obtained in Example 5 were analysed by ATR-FTIR after evaporating the solvent at 80° C. overnight. The absolute amount of PEO extracted was determined as depicted in formula 1. The relative amount of PEGDA in the extracts was related to the peak area of the ester carbonyl specific C=O str. band at 1730 cm$^{-1}$ of the normalised FTIR spectra. The peak area was calculated applying baseline points at 1753 and 1696 cm$^{-1}$ for the coatings and the dried extracts. The acrylate carbonyl band shifts slightly when the acrylates are polymerised. However, the baseline points were chosen in a way that unreacted as well as reacted acrylates are incorporated. The coating before extraction was used as a reference. The fraction PEGDA in the coating prior to extraction is 0.9.

The absolute amount of extracted PEO in percentage of the complete coating was calculated as follows:

$$PEO_{extracted}(\%) = m\% - \frac{m\% * [PEGDA]_{coating} * A_{extract}^{1730}}{A_{coating}^{1730}} \quad \text{(formula 1)}$$

Where:
m %=weight loss fraction as determined in example 5 (FIG. 2)
$[PEGDA]_{coating}$=PEGDA fraction in the coating (=0.9)
$A_{extract}^{1730}$=Peak area acrylate carbonyl band 1730 cm$^{-1}$ of the extract
$A_{coating}^{1730}$=Peak area acrylate carbonyl band 1730 cm$^{-1}$ of the coating The migrateable component was thus identified as the functional oligomer or polymer; in this case PEO. Only a very tiny fraction of the supporting polymer migrates out of the coating, as was to be expected, since it was already established (see above) that the acrylate conversion was already more than 95% after the first UV exposure. FIG. 3 shows that the absolute amount of PEO in the extracts decreases significantly when the solvent of the coating was evaporated between UV exposures.

Example 7

Synthesis of Urethane Diacrylate Oligomer 75.48 g (0.65 mol) hydroxy ethylacrylate (HEA) was added dropwise to 113.20 g (0.65 mol) 2,4-toluenedi-isocyanate (TDI) in the presence of 0.3 g (0.48 mmol) Dibutyl tin di laureate (DBTDL) or tin II ethyl hexanoate (0.5 g (1.3 mmol). The conversion of the isocyanate groups (NCO) was monitored by a titration. 174.95 g (0.60 mol) of this HEA-TDI mixture was added to 301.33 grams PTGL1000 from Hodogaya (0.60 mol OH) and 0.3 g Irganox 1035 and stirred. The temperature was gradually increased to 80° C. After 7 hours the NCO value was 0.026%. Overnight the reaction mixture cooled down till 50° C. After another 16 hours the NCO level was 0.007%. The yield of the urethane diacrylate oligomer was 450 g (92%.)

Example 8

Coating Formulation for Primer Coating (Primer A)

TABLE 3

| Materials | % w/w |
| --- | --- |
| Urethane acrylate oligomer (Example 7) | 47.00 |
| Ethoxylated nonyl phenol acrylate (Sartomer SR 504) | 8.00 |
| Lucirin TPO | 1.30 |
| Irgacure 184 (Ciba) | 3.00 |
| Irganox 1035 | 0.70 |
| Ethanol | 40.00 |
| Total | 100.00 |

The materials were mixed together to obtain a coating composition.

Example 9

Coating Formulation of Primer Coating (Primer B)

TABLE 4

| Materials | % w/w |
| --- | --- |
| Bisphenol A glycerolate (1Gly/Ph) diacrylate | 79.20 |
| Irgacure 2959 (Ciba) | 0.80 |
| Ethanol | 20.00 |
| Total weight of formulation | 100.00 |

The materials were mixed together to obtain a coating composition.

Example 10

Hydrophilic Top Coat A (PVP 360,000)

TABLE 5

| Materials | % w/w |
| --- | --- |
| PEG4000 diacrylate (Example 1) | 9.80 |
| PVP (K90) Mw 360 000 (Aldrich 43, 719-0) | 9.80 |
| 2-Hydroxy-4'-(2-hydroxyethoxy)-2-methylpropiophenone (Irgacure 2959) | 0.40 |
| Distilled water | 40.00 |
| Ethanol | 40.00 |

TABLE 5-continued

| Materials | % w/w |
|---|---|
| Total weight of formulation | 100.00 |

The materials were mixed together to obtain a coating composition.

Example 11

Hydrophilic Top Coat B (PVP 1,300000)

TABLE 6

| Materials | % w/w |
|---|---|
| PEG4000 diacrylate (Example1) | 9.80 |
| PVP (Mw) 1,300,000 (Aldrich 43,719-0). | 9.80 |
| 2-Hydroxy-4'-(2-hydroxyethoxy)-2-methylpropiophenone (Irgacure 2959) | 0.40 |
| Distilled water | 40.00 |
| Ethanol | 40.00 |
| Total weight of formulation | 100.00 |

The materials were mixed together to obtain a coating composition.

Example 12

Application of PES Primer onto a Guidewire Filament

A primer coating was applied on a stainless steel guide wire filament with a diameter of 165 µm with a coating dye. The primer (Du Pont, 420-810) 25 w % polyethersulphone in N-methylpyrollidone (NMP) was applied as described in U.S. Pat. No. 6,086,547 and J. Biomed. Mater. Res. (Appl. Biomaterials) 63: 692-698, 2002; and resulted in a coating thickness of 3-5 µm on the stainless steel wire. The oven temperature was 300° C. so as to remove the high boiling NMP solvent.

Example 13

Application of Photocurable Coatings onto Guidewire Filament

In order to be able to apply photocurable coatings, the filament coating line described in U.S. Pat. No. 6,086,547 and J. Biomed. Mater. Res. (Appl. Biomaterials) 63: 692-698, 2002; was retrofitted with UV lamps in between the coating die and oven as shown in FIG. 4, to give total illumination around a cylindrical geometry. A Fusion F600 lamp, D bulb (max. 240 W/cm2) fitted with a R500 reflector was used. When used in conjunction with the UV lamps, the oven temp was set to 150° C. The speed of the coating line was 70 m/min which resulted in a UV dose of 0.7 W/cm$^2$ (upon each pass under the UV lamps) and a residence time in the oven of 10 seconds after each UV exposure. The UV dose was measured using a Solatell™ Light meter fitted with a diffuser.

The UV primer coatings were applied (via a coating die) either directly onto steel filaments (diameter of 165 µm) or onto PES primer coated filaments that were coated according to example 12. The dry film thickness of the UV primer coatings was 1-3 micron.

The hydrophilic top coats A or B (Examples 10 or 11) were applied onto primer coated steel wire filaments in the same manner as described for the primer coating with the main difference that the hydrophilic coatings were passed multiple times (between 1 and 5) under the UV lamp (0.7 W/cm2/pass) and oven (150° C.). The dry lubricious coating had a thickness of 2-3 µm.

Example 14

Coiling of the Coated Wires

The multiple coated steel filaments according to example 13 were coiled with a typical winding angle of 80-85° on a stainless steel core wire of diameter of 0.43 mm using a spindle, connected to an electromotor with controllable speed as described in J. Biomed Mater Res (Appl Biomaterials) 63: 692-698, 2002.

The coated filaments coiled along the stainless steel core wire are further referred to as coated coils. These coated coils are used in the lubricity tests described below.

Example 15

Coated Coils Comprising Hydrophilic Top Coat B and Primer Coating B

The hydrophilic topcoat B as described in example 11 was applied onto a steel wire filament that was coated with primer B (as described in example 9) according to the procedure described in Example 13. The coated filament comprising the hydrophilic topcoat was passed three times through the UV and oven set-up to receive a total UV dose of 2.1 W/cm$^2$. The resultant filaments were coiled according to procedure described in Example 14.

Example 16

Guide Wire Coils Comprising Hydrophilic Top Coat A and Primer Coating A

PES primer was applied onto a steel wire filament as described in Example 12. On top of this primer another primer coating (Primer coating A, example 8) and the hydrophilic coating A (example 10) were applied according to the procedure described in Example 13. The resultant filaments were coiled according to procedure described in Example 14.

Example 17

Guide Wire Coils Comprising Hydrophilic Top Coat B and Primer Coating A

PES primer was applied onto a steel wire filament as described in Example 12. On top of this primer another primer coating (Primer coating A, example 8) and the hydrophilic coating B (example 11) were applied according to the procedure described in Example 13. The resultant filaments were coiled according to procedure described in Example 14.

Example 18

Test Methods for Measuring the Lubricious Properties of Coated Coils

A test method was developed to measure the lubricious properties of the coated coils as well as the wear resistance of the coated coils.

The coated coils were tested by moving them back and forth (push and pull) through a tightly fitting (Medtronic) PU-Pro-Flo, 6F pigtail catheter tube with an inner diameter of 1.27 mm which is approximately 400 to 500 micron more than the largest outer diameter of the coated coil. The catheter was gently curved (without kinking) into an arc by placing it into a polycarbonate mould of a half circle with a diameter of 40 mm. The catheter tube of 185±1 mm is aligned with one top of the mould while the other end of the catheter tube is used to support the coated coil over a longer distance. Care was taken to ensure that the end of the catheter tube did not abrade the coated coil. Both entrances of the catheter tube were therefore 'smoothened' and made circular by use of a blunt tip.

The mould and catheter tube were immersed in water at 23° C. Care was taken to ensure that the mould was at least 5 cm below the water surface to prevent formation of air bubbles in the catheter tube during the experiment. The catheter tube was then flushed with water, to ensure that there is no air entrapment in the catheter tube. The coated coil is guided manually through the catheter tube to ensure no bending and/or damage of the coated coils and attached to a tensiometer. The free end of the coated coil wire is cut, about 60 mm above the water level (see FIG. 5 for schematic representation of set-up).

The tests was performed using a Zwick Z050 tensile spindle tester. Control and analysis was performed with Zwick TestXpert v7.11 software. The coated coil was attached to a 20N load cell by a clamp with a clamping distance of ±50 mm. The test speed was 200 mm/min.

To determine the lubricious properties of the coated coil, the coated coil was pulled through the catheter tube with a displacement of 40 mm. After 5 seconds, the coated coil was pushed back again through the catheter tube with a displacement of 40 mm. This constituted one test cycle.

The lubricious properties of the coated coils were measured in terms of two parameters; the dynamic friction force and the static friction force (stiction). The static friction force is defined as the maximum force within the first 2 mm of displacement for the pull part of the cycle. The dynamic friction force is defined as the force measured at regular intervals over the test path of 2-40 mm for the pull part of the cycle. The ratio static friction/dynamic friction was determined by dividing the static friction force by the average friction force from 2 to 5 mm of displacement of the pull cycle.

Example 19

Comparative Example with a Commercially Available Lubricious Coating

Coated coils produced according to examples 15 and 16 were compared to coils coated with the commercially available product Slipskin™. These coils were obtained from MCTec (Medical Coating Technology, Venlo, The Netherlands) and manufactured as described in U.S. Pat. No. 6,086,547. These coils are hereinafter referred to as commercial product CP.

The measured friction forces of the pull part of the cycle were then plotted for each of the three coatings. FIG. 5 shows a comparison of representative examples for each of the three coils. The static friction force of the commercial product CP appeared to be the highest; about 340 mN. Both coatings prepared according to the invention had considerable lower dynamic friction forces; the coating according to example 16 had a static friction force of about 130 mN whereas the static friction force of the coating according to example 15 was barely distinguishable from the dynamic friction force; about 100 mN. (FIG. 5).

Example 20

Determination of the Wear Resistance of Coated Coils

The wear resistance of the coated coils was determined by repeating the test cycle as described in example 18 at different time intervals. This was done by performing 8 consecutive test cycles with 5 seconds waiting time between each cycle, after 15 minutes followed by a series of 5 consecutive cycles with again 5 seconds waiting time in between. The series of 5 consecutive cycles was then repeated for a number of times, each time with 15 minutes waiting time in between a series.

Coated coils prepared according to examples 16 and 17 were compared to commercial product CP. The ratio static friction/dynamic friction was determined for each cycle as described in example 18. Each data point in FIG. 6 represents the ratio static friction/dynamic friction of a single cycle in the wear resistance set-up as described herein above, note that the X-axis in FIG. 6 does not have a linear or continuous scale. Since it appeared that there was quite a variation between the wear resistances of the individual coils of the commercial product CP, two comparative examples are shown in FIG. 6; an averagely performing specimen (squares) and a best performing specimen (diamonds) of the commercial product. In comparison, the ratio static friction/dynamic friction of 2 representative examples of coils coated according to the invention is shown.

The data obtained with the coils coated according to the invention as described in examples 16 and 17 appeared to be more constant over time. The large variation in the ratio's obtained with the commercial samples appears mainly due to a large variation in their static friction, whereas their dynamic friction was relatively constant, however nearly doubled in the course of the experiment. In contrast, the static as well as dynamic friction values obtained with the coatings according to the invention were both remarkably constant. From these data it is obvious that the coefficient of variation of the ratio static/dynamic friction of a coating according to the invention is well below 9 whereas this coefficient of variation for prior art coatings is well above 17.

The data obtained in the above-described experimental set-up are shown in table 7.

TABLE 7

Average static (S) friction forces and dynamic (D) friction forces of 53 consecutive cycles performed on 4 different coatings as detailed in Example 20. Average and Standard deviations (SD) are given at the bottom of the table as well as the coefficient of variation (COV)

| Cycle | Representative CP | | | Best performing CP | | | Example 16 coating | | | Example 17 coating | | |
|---|---|---|---|---|---|---|---|---|---|---|---|---|
| | S | D | S/D | S | D | S/D | S | D | S/D | S | D | S/D |
| 1 | 421.37 | 93.98 | 4.48 | 317.75 | 221.8 | 1.43 | 319.4 | 228.54 | 1.40 | 337.96 | 252.33 | 1.34 |
| 2 | 257.28 | 86.24 | 2.98 | 60.05 | 69.94 | 0.86 | 132.06 | 77.46 | 1.70 | 209.94 | 127.54 | 1.65 |
| 3 | 312.72 | 85.3 | 3.67 | 63.69 | 55.78 | 1.14 | 127.79 | 69.76 | 1.83 | 231.92 | 125.71 | 1.84 |
| 4 | 322.85 | 86.95 | 3.71 | 167.59 | 61.25 | 2.74 | 125.12 | 70.06 | 1.79 | 236.01 | 130.26 | 1.81 |
| 5 | 311.51 | 88.86 | 3.51 | 188.32 | 53.55 | 3.52 | 123.07 | 69.21 | 1.78 | 244.73 | 136.41 | 1.79 |
| 6 | 281.93 | 92.03 | 3.06 | 214.03 | 56.94 | 3.76 | 124.76 | 68.52 | 1.82 | 223.64 | 140.99 | 1.59 |
| 7 | 364.19 | 95.45 | 3.82 | 227.9 | 55.97 | 4.07 | 114.44 | 67.99 | 1.68 | 244.46 | 144.14 | 1.70 |
| 8 | 331.67 | 98.01 | 3.38 | 239.38 | 53.6 | 4.47 | 114.88 | 67.59 | 1.70 | 246.15 | 146.74 | 1.68 |
| 9 | 333.57 | 88.57 | 3.77 | 280.83 | 62.61 | 4.49 | 146.76 | 79.25 | 1.85 | 260.83 | 152.29 | 1.71 |
| 10 | 278.21 | 84.99 | 3.27 | 236.71 | 57.07 | 4.15 | 122.19 | 72.01 | 1.70 | 253.27 | 147.99 | 1.71 |
| 11 | 336.42 | 83.86 | 4.01 | 270.6 | 52.39 | 5.17 | 112.14 | 72.54 | 1.55 | 253.62 | 151.28 | 1.68 |
| 12 | 343.95 | 85.55 | 4.02 | 273.27 | 59.86 | 4.57 | 119.17 | 73.81 | 1.61 | 252.02 | 153.68 | 1.64 |
| 13 | 335.04 | 90.99 | 3.68 | 240.71 | 59.18 | 4.07 | 119.7 | 75.08 | 1.59 | 257.89 | 156.76 | 1.65 |
| 14 | 352.43 | 89.55 | 3.94 | 272.11 | 64.86 | 4.20 | 127.53 | 82.79 | 1.54 | 267.94 | 157.68 | 1.70 |
| 15 | 258.48 | 88.47 | 2.92 | 257.88 | 56.16 | 4.59 | 117.57 | 76.73 | 1.53 | 260.29 | 161.97 | 1.61 |
| 16 | 330.45 | 90.25 | 3.66 | 265.62 | 52.45 | 5.06 | 118.63 | 77.71 | 1.53 | 264.21 | 165.69 | 1.59 |
| 17 | 267.83 | 92.42 | 2.90 | 270.16 | 60.47 | 4.47 | 122.91 | 78.39 | 1.57 | 250.69 | 168.23 | 1.49 |
| 18 | 262.12 | 96.8 | 2.71 | 244.8 | 62.69 | 3.90 | 119.52 | 78.94 | 1.51 | 259.85 | 169.37 | 1.53 |
| 19 | 393.87 | 99.51 | 3.96 | 397.26 | 68.15 | 5.83 | 151.24 | 87.86 | 1.72 | 279.14 | 169.25 | 1.65 |
| 20 | 269.74 | 99.93 | 2.70 | 254.5 | 63.32 | 4.02 | 113.61 | 81.86 | 1.38 | 267.58 | 172.86 | 1.55 |
| 21 | 282.28 | 105.24 | 2.68 | 248.36 | 65.16 | 3.81 | 121.69 | 82.82 | 1.47 | 274.6 | 175.65 | 1.56 |
| 22 | 298.72 | 109.57 | 2.73 | 321.21 | 64.01 | 5.02 | 126.23 | 82.38 | 1.53 | 276.2 | 177.53 | 1.56 |
| 23 | 295.6 | 115.97 | 2.55 | 334.64 | 62.84 | 5.33 | 100.42 | 83.08 | 1.21 | 274.07 | 180.33 | 1.52 |
| 24 | 422.41 | 114.22 | 3.70 | 382.15 | 70.78 | 5.40 | 125.46 | 91.68 | 1.37 | 245.34 | 178.01 | 1.38 |
| 25 | 328.12 | 114.63 | 2.86 | 194.46 | 64.59 | 3.01 | 126.88 | 86.09 | 1.47 | 243.65 | 181.1 | 1.35 |
| 26 | 300.7 | 117.33 | 2.56 | 294.17 | 67.06 | 4.39 | 126.97 | 87.15 | 1.46 | 246.05 | 183.44 | 1.34 |
| 27 | 296.12 | 119.61 | 2.48 | 317.12 | 71.11 | 4.46 | 114.24 | 87.64 | 1.30 | 279.59 | 186.67 | 1.50 |
| 28 | 271.46 | 124.49 | 2.18 | 323.62 | 64.52 | 5.02 | 122.97 | 88.68 | 1.39 | 277.81 | 188.52 | 1.47 |
| 29 | 250.36 | 123.87 | 2.02 | 434 | 72.81 | 5.96 | 147.53 | 96.77 | 1.52 | 300.94 | 188.67 | 1.60 |
| 30 | 391.79 | 122.42 | 3.20 | 340.78 | 72.68 | 4.69 | 123.68 | 91.03 | 1.36 | 257.44 | 190.49 | 1.35 |
| 31 | 313.07 | 123.68 | 2.53 | 355.99 | 75.1 | 4.74 | 131.95 | 91.17 | 1.45 | 284.48 | 194.12 | 1.47 |
| 32 | 336.51 | 125.85 | 2.67 | 374.32 | 77.1 | 4.85 | 138.18 | 91.85 | 1.50 | 273.54 | 194.83 | 1.40 |
| 33 | 355.63 | 127.25 | 2.79 | 390.33 | 78.12 | 5.00 | 139.61 | 92.63 | 1.51 | 258.24 | 197.54 | 1.31 |
| 34 | 426.47 | 124.28 | 3.43 | 499.4 | 86.2 | 5.79 | 144.74 | 100.66 | 1.44 | 308.06 | 196.33 | 1.57 |
| 35 | 395.76 | 125.84 | 3.14 | 313.4 | 82.86 | 3.78 | 140.47 | 94.71 | 1.48 | 292.04 | 200.4 | 1.46 |
| 36 | 376.21 | 127.66 | 2.95 | 313.58 | 86.08 | 3.64 | 133.79 | 94.82 | 1.41 | 290.71 | 203.38 | 1.43 |
| 37 | 394.46 | 133.44 | 2.96 | 374.24 | 89.88 | 4.16 | 133.17 | 95.1 | 1.40 | 291.51 | 204.53 | 1.43 |
| 38 | 405.97 | 137.76 | 2.95 | 395.06 | 88.42 | 4.47 | 133.44 | 95.14 | 1.40 | 294 | 207.14 | 1.42 |
| 39 | 425.95 | 137.21 | 3.10 | 469.06 | 95.61 | 4.91 | 148.65 | 102.99 | 1.44 | 310.81 | 205.85 | 1.51 |
| 40 | 391.09 | 140.02 | 2.79 | 330.83 | 95.71 | 3.46 | 124.27 | 96.04 | 1.29 | 295.42 | 208.82 | 1.41 |
| 41 | 371.8 | 143.86 | 2.58 | 356.63 | 101.07 | 3.53 | 137.44 | 96.72 | 1.42 | 282.79 | 211.68 | 1.34 |
| 42 | 422.41 | 144.46 | 2.92 | 393.72 | 109.49 | 3.60 | 140.2 | 97.97 | 1.43 | 273.01 | 212.98 | 1.28 |
| 43 | 418.86 | 147.83 | 2.83 | 431.44 | 114.71 | 3.76 | 135.75 | 97.56 | 1.39 | 300.41 | 215.54 | 1.39 |
| 44 | 291.87 | 145.34 | 2.01 | 502.92 | 122.53 | 4.10 | 156.07 | 106.45 | 1.47 | 319.61 | 213.48 | 1.50 |
| 45 | 421.54 | 147.36 | 2.86 | 376.61 | 120.69 | 3.12 | 138.45 | 100.3 | 1.38 | 292.92 | 215.55 | 1.36 |
| 46 | 358.82 | 152.06 | 2.36 | 418.86 | 125.34 | 3.34 | 144.06 | 101.74 | 1.42 | 278.86 | 219.01 | 1.27 |
| 47 | 325.26 | 155.59 | 2.09 | 457.38 | 129.51 | 3.53 | 122.52 | 101.69 | 1.20 | 284.29 | 220.71 | 1.29 |
| 48 | 348.53 | 157.25 | 2.22 | 467.07 | 134.33 | 3.48 | 141.57 | 102.24 | 1.38 | 302.7 | 220.99 | 1.37 |
| 49 | 491.6 | 153.36 | 3.21 | 503.49 | 130.41 | 3.86 | 148.79 | 110.45 | 1.35 | 293.91 | 220.56 | 1.33 |
| 50 | 423.44 | 152.98 | 2.77 | 426.46 | 123.7 | 3.45 | 140.33 | 103.49 | 1.36 | 308.59 | 225.6 | 1.37 |
| 51 | 421.62 | 153.75 | 2.74 | 455.28 | 128.3 | 3.55 | 140.42 | 104.21 | 1.35 | 308.24 | 227.48 | 1.36 |
| 52 | 421.27 | 155.66 | 2.71 | 467.2 | 134.16 | 3.48 | 146.47 | 105.04 | 1.39 | 309.66 | 228.18 | 1.36 |
| 53 | 395.32 | | | 483.39 | 138.68 | 3.49 | 133.84 | 105.47 | 1.26 | 306.1 | 230.21 | 1.33 |
| Average | | | 2.93 | | | 4.30 | | | 1.46 | | | 1.47 |
| SD | | | 0.54 | | | 0.76 | | | 0.12 | | | 0.13 |
| COV | | | 18.3% | | | 17.6% | | | 8.5% | | | 8.7% |

Example 21

Wear Resistance at Different Time Intervals

Another series of experiments was performed to determine the wear resistance with different waiting times between a series of cycles. The experimental set-up is considered to mimic the circumstances under which a coated coil such as in a guide wire or catheter would be used in practice. This was done by performing 3 consecutive test cycles with 5 seconds waiting time between each cycle, after an increasing amount of time followed by a series of again 3 consecutive cycles with again 5 seconds waiting time in between. The waiting time in between the series of 3 cycles increased from 0.5 via 1, 2, 4, 8, 15 and 30 to 60 minutes. After this series of experiments, the whole procedure was repeated once again, starting again with a waiting time of 0.5 minutes increasing to 60 minutes. The results obtained with a coating obtained with a process according to the invention as exemplified in example 16 in comparison to a commercial product are depicted in FIG. 7.

It can be seen in FIG. 7 that the dynamic friction of the commercial product increased already after the first series of 3 cycles and steadily increased thereafter, whereas the dynamic friction of the coil coated according to the invention remained remarkably stable during the whole course of the experiment, i.e. more than 4 hours. Lowest/highest values obtained with a commercial coating from the prior art were 36/186 (average 94), whereas lowest/highest values obtained with a coating according to the invention were 78 and 88 (average 79, see table 8).

TABLE 8

| Cycle # | Best performing CP | Example 16 coating |
| --- | --- | --- |
| 1 | 59.79 | 88.08 |
| 2 | 38.93 | 81.56 |
| 3 | 37.28 | 79.79 |
| 4 | 41.7 | 79.68 |
| 5 | 36.92 | 78.45 |
| 6 | 36.04 | 79.62 |
| 7 | 41.46 | 79.98 |
| 8 | 37.68 | 80.67 |
| 9 | 38.25 | 80.66 |
| 10 | 45.72 | 79.34 |
| 11 | 41.02 | 77.9 |
| 12 | 42.55 | 77.78 |
| 13 | 50.56 | 77.12 |
| 14 | 47.04 | 75.1 |
| 15 | 48.56 | 76.39 |
| 16 | 58.44 | 75.12 |
| 17 | 53.72 | 75.42 |
| 18 | 55.81 | 76.73 |
| 19 | 67.18 | 75.72 |
| 20 | 64.62 | 74.46 |
| 21 | 67.08 | 75.84 |
| 22 | 77.82 | 75.6 |
| 23 | 74.67 | 73.82 |
| 24 | 77.83 | 76.16 |
| 25 | 90.07 | 77.87 |
| 26 | 86.44 | 76.14 |
| 27 | 89.91 | 74.91 |
| 28 | 97.58 | 79.08 |
| 29 | 96.46 | 75.98 |
| 30 | 99.18 | 76.82 |
| 31 | 104.18 | 80.01 |
| 32 | 103.05 | 76.72 |
| 33 | 106.05 | 76.71 |
| 34 | 114.75 | 80.02 |
| 35 | 112.97 | 77.4 |
| 36 | 115.42 | 76.71 |
| 37 | 124.5 | 81.21 |
| 38 | 123.36 | 77.82 |
| 39 | 126.97 | 77.61 |
| 40 | 138.13 | 81.94 |
| 41 | 136.32 | 77.71 |
| 42 | 143.07 | 78.2 |
| 43 | 155.22 | 82.45 |
| 44 | 153.69 | 78.16 |
| 45 | 156.64 | 77.54 |
| 46 | 167.81 | 81.79 |
| 47 | 166.23 | 77.36 |
| 48 | 171.55 | 77.4 |
| 49 | 181.07 | 80.03 |
| 50 | 181.34 | 76.59 |
| 51 | 186.42 | 77.48 |
| Average | 94.19 | 77.89 |
| SD | 47.06 | 2.11 |
| COV | 50.0% | 2.7% |

Table 8. Values plotted in FIG. 7

Eventually, the dynamic friction of the commercial product increased more than 5-fold over the course of the experiment. It is therefore concluded that a coil coated according to the invention has an improved wear resistance in comparison to the commercial product CP. This contributes significantly to the reliability of a medical device coated with a coating according to the invention, such as a guidewire or a catheter, in the way that its lubricity is constant over the period that it is used, whereas a coating according to the prior art requires an ever increasing force over the course of the procedure on top of the disadvantage that a coating according to the prior art exhibits an unpredictable static friction after each period of resting, as exemplified in FIG. 6 and table 7.

Example 22

Comparison to a Coating Consisting of a Semi-IPN

A comparison was made between the amount of migrateables of a coating according to the invention and a coating based on a semi-interpenetrating network (IPN). To that end, a 200 um-thick layer of a coating composition according to table 10 (hydrophilic top coat A) was applied onto a glass plate. The composition was exposed to UV light followed by evaporation essentially as described in example 4. After 3 cycles of UV and heat, the coating composition was left overnight in the dark before extraction studies were performed. For comparison, a coating consisting of a semi-interpenetrating network was prepared essentially as described in U.S. Pat. No. 6,238,799. In more detail: a coating composition according to table 9 was prepared.

TABLE 9

| | |
| --- | --- |
| Polyurethane R-988 (Neoresins) eq. wt 2954 g/eq | 2.0 g |
| Polyvinylpyrrolidone Mwt 1,300,000 | 2.0 g |
| Cymel 303 MF-crosslinker (Cytec Corp.) | 0.090 g |
| Demineralized water | 36 g |

A wet 120 micrometer thick coating according to table 9 was applied on a glass plate and cured at 165° C. (325° F.) for 15 minutes as described in U.S. Pat. No. 6,238,799.

To study the amount of migrateables from each coating, the coatings were removed from the glass plate and weighed in a cellulose extraction thimble. The thimble was placed in a metal mesh holder with mesh size 1 mm$^2$. The metal holder including the thimble and coating was dried for 12 hours at 105° C. under reduced pressure and nitrogen flow (100 mbar). The metal holders were then immersed in 200 ml demineralised water for 16 hours at 37° C. under continuous stirring with a magnetic stirrer. The residual coating in the metal mesh holder was then dried for 12 hours at 105° C. under reduced pressure and nitrogen flow (100 mbar). The weight loss of the coating was determined by measuring the weight difference of the metal holder before and after extraction.

It was found that the coating according to the invention lost 1.8% of its weight whereas the semi-IPN coating according to U.S. Pat. No. 6,238,799 lost 7.1% of its weight. It is therefore concluded that a coating consisting of a semi-interpenetrating network has much more migrateables than a coating according to the invention.

Example 22

The Functional Polymer Becomes Covalently Attached to the Supporting Polymer Via the Network Bound Chromophore Derived from the Norrish Type I Photoinitiator In order to prove the photografting mechanism and that it originates from the chromophore that attaches to the cross-linked network in the photoinitiation process, the consumption of the chromophore absorbance was monitored together with the increase in crosslink density (determined by proton NMR T2 relaxation experiments.

Hydrophilic coating formulation of example 11 was applied onto glass with a 24 micron doctor blade as described in Example 4. The resultant dry film thickness was 5 micron. FT-IR analysis revealed an acrylate conversion of >96%.

Crosslink density in polymers was determined by solid state NMR $T_2$ relaxation experiment (Litvinov, and Dias, Macromolecules, 34, 4051-4060 (2001). Proof of new extra crosslinks which support the mechanism shown in FIG. 8 can be obtained by determining the crosslink density using ssNMR T2 relaxation experiments and also monitoring the consumption of the arylcarbonyl by UV spectroscopy as shown FIG. 9. NMR relaxation experiments were performed as described in V. M. Litvinov, Characterization of Chemical and Physical Networks in Rubbery Materials Using Proton NMR Magnetization Relaxation in "*Spectroscopy of Rubbery Materials*", V. M. Litvinov, P. P. De, Eds., RAPRA Technology, Shawbury, p. 353-400 (2002). For NMR experiments, cured coatings were removed from the glass plate and placed in an NMR tube. The measurement was performed for static tube with the samples at 70° C. Proton NMR $T_2$ relaxation experiment was performed with a low-field NMR spectrometer operating of a proton resonance frequency of 20 MHz. The decay of the transverse magnetization relaxation, $T_2$ relaxation decay, was measured with the Hahn-echo pulse sequence. (E. Hahn, *Physical Review*, 80, 580 (1950). The characteristic decay time, as determined by $T_2$ value, was determined by a list-squares fit of the $T_2$ relaxation decay using the following equation:

$$A(\tau)=A(0)\exp[-(\tau/T_2)]$$

where $A(0)$ and $A(\tau)$ is the signal amplitude at time zero and $\tau$

The NMR $T_2$ relaxation experiments show that PVP and PEG4000DA are well phase separated in all coatings. The phase separation was also determined by dynamic mechanical thermal analysis (DMTA) and atomic force microscopy (AFM). The NMR method enables selective determination of $T_2$ relaxation time for cured crosslinked polyethyleneglycol diacrylate, since the signal from PVP phase decreases nearly to zero much faster compared to PEG.

The experiment shows that $T_2$ relaxation time decreases with increasing the total UV- and IR-dose (FIG. 10). Since shorter $T_2$ relaxation time corresponds to lower molecular mass of network chains (i.e higher crosslink density). The results in FIG. 10 show that the crosslink density in PEG4000DA phase increases when a coating is subjected to multiple cross-linking steps separated by evaporation of the solvent. Since conversion of double bonds of acrylic chain-ends of PEG4000DA is nearly complete for all coatings (above 96±3%), the additional crosslinking is caused by another mechanism then that which arises from possible crosslinking of residual unreacted acrylate.

A coating applied as described above was analysed by UV spectroscopy using the Perkin Elmer Lambda 40. The absorbance ratio, of the phenyl groups at 254 nm relative to the UV absorbance of the phenyl group conjugated to the carbonyl at 279 nm was determined.

These ratios are given in the table 10 below.

TABLE 10

Absorbance ratios of 5 micron thick film

| UV and heat exposures | Absorbance ratio 254 nm/279 nm |
|---|---|
| UV only | 0.687 |
| UV/IR/UV/IR | 0.706 |
| UV/IR/UV/IR/UV/IR | 0.787 |

The actual UV spectra are shown in FIG. 9.

The results from Table 10 and FIG. 9 show that the UV absorbance ratio (254 nm/279 nm) increases when the coating is subjected to an evaporation step followed by UV treatment and that the UV absorbance ratio (254 nm/279 nm) increases even further when this procedure is repeated. The experiment also shows a loss of the absorption of the phenyl ring conjugated with the carbonyl group. This again supports the proposed mechanism given in FIG. 8.

The value of the UV absorbance ratio (254 nm/279 nm) increases with cross-link density (1/T2) as shown in FIG. 11.

Thus, taken together, the results of IR- and UV-spectroscopy, proton NMR $T_2$ relaxation analysis and the extraction study prove that due to the process according to the invention, the functional polymer (in this case PVP chains) were actually covalently crosslinked to the supporting polymer network (in this case PEG4000DA) via the network bound chromophore derived from the Norrish type I photoinitiator.

The invention claimed is:

1. A process for obtaining a coating comprised of a functional oligomer or polymer covalently linked to a polymerized supporting polymer, the process comprising subjecting a coating composition comprising a supporting monomer, oligomer or polymer; a functional oligomer or polymer; and a photoinitiator to photopolymerization conditions sufficient to covalently link the functional polymer or oligomer to the polymerized supporting polymer, wherein the photoinitiator in the coating composition consists of one or more Norrish type 1 photoinitiators that are not bound to the supporting monomer, oligomer or polymer or to the functional polymer or oligomer, and wherein the one or more photoinitiators (i) initiate polymerization of the supporting monomer, oligomer or polymer in a photoinitiation reaction to produce the polymerized supporting polymer, (ii) become bound to the supporting monomer, oligomer or polymer via initiation of polymerization of the supporting monomer, oligomer or polymer, and thereafter (iii) induce polymer cross-links between the supporting monomer, oligomer or polymer and the functional oligomer or polymer through a hydrogen abstraction mechanism when the one or more photoinitiators are bound to the supporting monomer, oligomer or polymer via initiation of polymerization of the supporting monomer, oligomer or polymer.

2. The process according to claim 1, wherein the coating composition comprises:
   at least one supporting monomer, oligomer or polymer capable of forming a supporting polymer network;
   at least one functional oligomer or polymer; and
   the photoinitiator.

3. The process according to claim 1, comprising the steps of:
   providing a surface;
   providing at least one supporting monomer, oligomer or polymer capable of forming a network;
   providing at least one functional oligomer or polymer;
   providing the photoinitiator;

mixing the at least one supporting monomer, oligomer or polymer with the at least one functional oligomer or polymer and the photoinitiator with a suitable solvent in order to obtain a coating composition;

applying the coating composition to the surface; and exposing the coating composition on the surface to an energy source thereby inducing polymerization of the at least one supporting monomer, polymer or oligomer, wherein the photoinitiator initiates polymerisation of the supporting monomer, oligomer or polymer in order to form a network and then generates extra cross-links with the functional oligomer or polymer by a hydrogen abstraction reaction.

4. The process according to claim 1, comprising the steps of:

providing a surface;

providing at least one supporting monomer, oligomer or polymer capable of forming a network;

providing at least one functional oligomer or polymer;

providing the photoinitiator;

mixing the at least one supporting monomer, oligomer or polymer with the at least one functional oligomer or polymer and the photoinitiator with a suitable solvent in order to obtain a coating composition;

applying the coating composition to the surface;

exposing the coating composition on the surface to an energy source thereby initiating polymerization of the at least one supporting monomer, polymer or oligomer;

evaporating the solvent; and exposing the coating composition on the surface to the energy source at least once again.

5. The process according to claim 4, wherein the step of evaporating the solvent is repeated at least once after the last exposure of the coating composition to the energy source.

6. The process according to claim 4, wherein the functional polymer or oligomer is a hydrophilic polymer or oligomer.

7. The process according to claim 6, wherein the surface is a surface of a medical device.

8. The process according to claim 1, wherein the functional polymer or oligomer is a hydrophilic polymer or oligomer.

9. The process according to claim 8, wherein the hydrophilic polymer or oligomer is chosen from the group consisting of poly(lactams), homo and copolymers of acrylic and methacrylic acid, polyvinyl alcohol, polyvinylethers, maleic anhydride based copolymers, polyesters, vinylamines, polyethyleneimines, polyethyleneoxides, poly(carboxylic acids), polyamides, polyanhydrides, polyphosphazenes, cellulosics, heparin, dextran, chondroitin sulphate, polypeptides, polysacharrides and polyesters.

10. The process according to claim 8, further comprising the step of applying the coating composition on a surface of a medical device.

11. The process according to claim 1, wherein the supporting polymer is chosen from the group consisting of polyethers, poly(meth)acrylates, polyurethanes, polyethylene and polypropylene co-difunctional polymers, polyvinyl chlorides, epoxides, polyamides, polyesters and alkyd copolymers.

12. The process according to claim 1, wherein the supporting polymer comprises a functional moiety that is chosen from the group consisting of amino, amido, sulphhydryl (SH), unsaturated esters, ethers and amides, and alkyd/dry resins.

13. The process according to claim 1, wherein the Norrish Type I photoinitiator is chosen from the group consisting of benzoin derivatives, methylolbenzoin and 4-benzoyl-1,3-dioxolane derivatives, benzilketals, $\alpha,\alpha$-dialkoxyacetophenones, $\alpha$-hydroxy alkylphenones, $\alpha$-aminoalkylphenones, acylphosphine oxides, bisacylphosphine oxides, acylphosphine sulphides, and halogenated acetophenone derivatives.

14. The process according to claim 1, which comprises applying the coating composition on a surface of a medical device.

15. The process according to claim 14, wherein the medical device is chosen from the group consisting of catheters, guidewires, stents, metal and plastic implants, contact lenses and medical tubing.

16. The process according to claim 1, wherein the photoinitiator comprises (2-hydroxy-4'-(2-hydroxyethoxy)-2-methyl propiophenone).

17. A process to induce polymer cross-linking of a functional oligomer or polymer to a polymerized supporting polymer comprising: providing a reaction mixture comprised of the functional oligomer or polymer and a supporting monomer, oligomer or polymer, incorporating into the reaction mixture a photoinitiator consisting of a Norrishtype 1 photoinitiator that is not bound to the supporting monomer, oligomer or polymer or to the functional polymer or oligomer, and subjecting the reaction mixture to cross-linking conditions to cause the photoinitiator to (i) initiate polymerization of the supporting monomer, oligomer or polymer in a photoinitiation reaction, to produce the polymerized supporting polymer, (ii) become bound to the supporting monomer, oligomer or polymer via initiation of polymerization of the supporting monomer, oligomer or polymer, and thereafter (iii) induce cross-linking of the functional oligomer or polymer to the polymerized supporting polymer through a hydrogen abstraction mechanism by the photoinitiator that is bound to the supporting monomer, oligomer or polymer via initiation of polymerization of the supporting monomer, oligomer or polymer.

18. A coating obtained by a process according to claim 1.

19. A medical device comprising a coating according to claim 18.

20. The medical device according to claim 19, chosen from the group consisting of catheters, guidewires, stents, metal and plastic implants, contact lenses and medical tubing.

* * * * *